US006800454B2

(12) United States Patent
Ma et al.

(10) Patent No.: US 6,800,454 B2
(45) Date of Patent: Oct. 5, 2004

(54) NUCLEIC ACID MOLECULE ENCODING CHEMOKINE-LIKE FACTOR 1 (CKLF1)

(75) Inventors: Dalong Ma, Beijing (CN); Wenling Han, Beijing (CN); Yingmei Zhang, Beijing (CN); Quansheng Song, Beijing (CN); Chunhui Di, Beijing (CN); Jiaqiang Huang, Beijing (CN); Jian Tang, Beijing (CN); Guanghui Chen, Beijing (CN)

(73) Assignees: Beijing Medical University, Beijing (CN); Beijing Medical University United Biological Engineering Company, Beijing (CN)

( * ) Notice: Subject to any disclaimer, the term of this patent is extended or adjusted under 35 U.S.C. 154(b) by 7 days.

(21) Appl. No.: 09/801,115

(22) Filed: Mar. 7, 2001

(65) Prior Publication Data

US 2002/0001828 A1 Jan. 3, 2002

Related U.S. Application Data

(63) Continuation-in-part of application No. PCT/CN00/00026, filed on Feb. 15, 2000, now abandoned.

(30) Foreign Application Priority Data

May 14, 1999 (CN) ........................................ 99107284 A

(51) Int. Cl.$^7$ ......................... C07H 21/04; C12P 21/00; C12N 15/09; C07K 14/00
(52) U.S. Cl. .................. 435/69.1; 435/70.1; 435/252.3; 435/320.1; 435/325; 435/235.1; 435/254.11; 530/300; 536/23.1; 536/23.5
(58) Field of Search .............................. 536/23.1, 23.5; 530/300, 350; 435/69.1, 70.1, 252.3, 320.1, 325, 235.1, 254.11

(56) References Cited

U.S. PATENT DOCUMENTS 5,656,724 A   8/1997   Daly et al. ................... 530/324
5,789,539 A   8/1998   Daly et al. ................... 530/324

FOREIGN PATENT DOCUMENTS

| CN | 1202906 | 12/1998 |
|---|---|---|
| EP | 0860446 A1 | 8/1998 |
| WO | WO 94/01548 | * 1/1994 |
| WO | WO 96/13587 | 5/1996 |

OTHER PUBLICATIONS

Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Han et al. Molecular cloning and characterization of chemokine–like factor 1 (CKLF1), a novel human cytokine with unique structure and potential chemotactic activity. Biochem J. 357(Pt 1):127–35, 2001.*
NCI–CGAP. Genbank Accession No. AI078580, EST database, Aug. 10, 1998.*
Hillier et al. Genbank Accession No. AA455042, EST database, Jun. 6, 1997.*
Alberts et al. Molecular Biology of the Cell, New York: Garland Publishing, 1994; p. 106–110, Figure 3–16, 230–234.*
Baggiolini et al., 1997 "Human Chemokines: An Update", Annu. Rev. Immunol. 15:675–705.
Cocchi et al., 1995, "Identification of RANTES, MIP–1α, and MIP–1β as the Major HIV–Suppressive Factors Produced by CD8+ T Cells", Science 270:1811–15.
Diatchenko et al., 1996, "Suppression subtractive hybridization: A method for generating differentially regulated or tissue–specific cDNA probes and libraries", Proc. Natl. Acad. Sci. USA 93:6025–30.
Hsu et al., 1990, "Expression of Interleukin–10 Activity by Epstein–Barr Virus Protein BCRF1", Science 250:830–32.
Ma et al., 1991, "The Expression of Human Recombinant Interleukin–3 Containing a Cleavage Sequence for Thrombin in *E.coli*", Journal of Beijing Medical University 11:26–29.
Brantschen et al. 1989, "Differential Expression of Cytokine mRNAs in Human Cell Lines", Lymphkine Research, 2(3) 163–72.
Marshall et al., 1998 "HGS launches "first" genomics product in clinic", Nature Biotechnology, 16 (2): 120.

* cited by examiner

*Primary Examiner*—Elizabeth Kemmerer
*Assistant Examiner*—Bridget E. Bunner
(74) *Attorney, Agent, or Firm*—Yi Li

(57) ABSTRACT

The present invention provides chemokine-like factor (CKLF) polypeptides with chemotactic and hematopoietic stimulating activities and polynucleotides encoding such polypeptides. Additionally, a method for producing such CKLF polypeptides by recombinant techniques is provided. Also provided are the antibodies and antagonists against such polypeptides. The present invention further disclose a drug compound comprising a therapeutically effective amount of such CKLF polypeptides as well as pharmaceutically acceptable excipients and carriers. Also disclosed are the uses of such CKLF polypeptides and polynucleotides in diagnostics or therapeutics to treat immunodeficiency, hematopoietic diseases and primary tumors.

23 Claims, 18 Drawing Sheets

Land 1:G3PDH; lane 2: U1; lane 3 : CKLF1; lane 4:U14; lane 5: U24.
In each lane, the left is total RNA from tester and the right is total RNA from driver.

Lane 1: marker; lane 2: uninduced E.coli; lane 3: induced E.coli; lane 4: inclusion body after lysed with ultrasonic; lane 5: denatured inclusion body

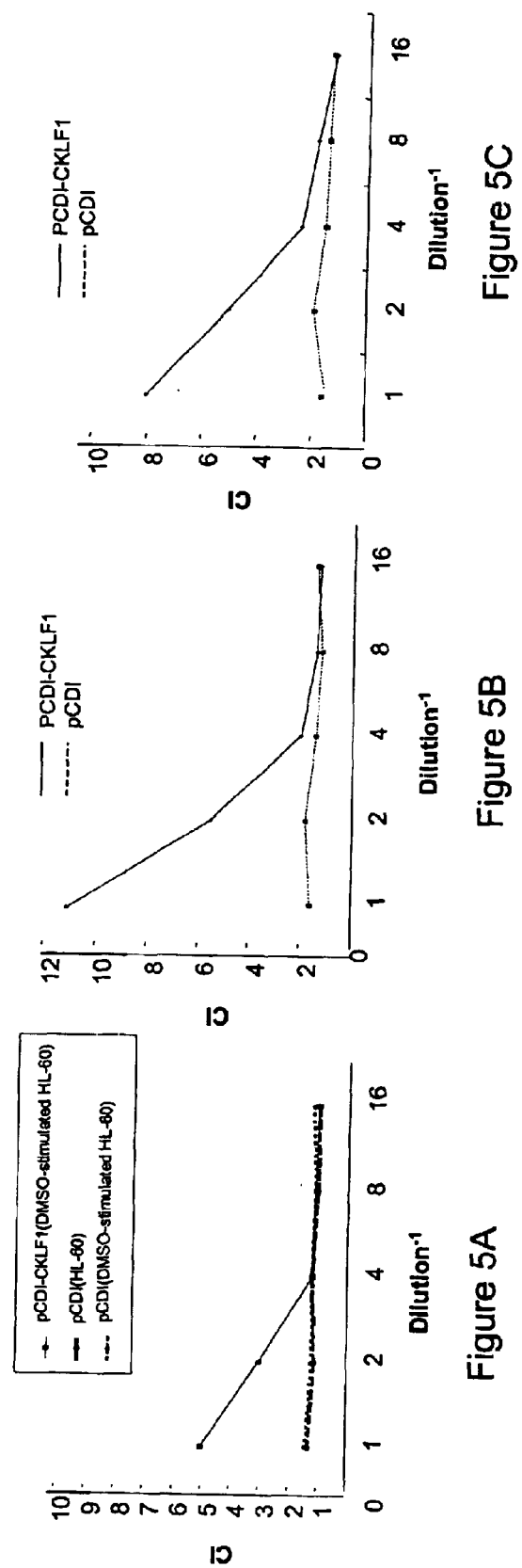

1.PCR marker, 2. Negative control, 3. brain, 4.colon, 5. heart,
6. kidney, 7. leukocyte, 8. liver, 9. lung, 10. ovary 1. PCR marker, 2. Negative control, 3. pancreas, 4. placenta, 5. prostate, 6.skeletal muscle, 7.intestine, 8. spleen, 9.testis, 10.thymus 1. PCR marker, 2. Negative control, 3. Fetal brain, 4. Fetal heart, 5. Fetal kidney, 6. Fetal liver, 7. Fetal lung, 8. Fetal muscle, 9. Fetal spleen, 10. Fetal thymus 1. PCR marker, 2. Negative control, 3. Breast carcinoma, 4. Colon adenocarcinoma(CX-1)
5. Colon adenocarcinoma(G1-112), 6. Lung carcinoma(G1-117), 7. Lung carcinoma(LX-1)
8. ovarian carcinoma, 9. Pancreas carcinoma, 10. Prostatic carcinoma

SEQUENCE LISTING

<160> NUMBER OF SEQ ID NOS: 8

<210> SEQ ID NO 1
<211> LENGTH: 534
<212> TYPE: DNA
<213> ORGANISM: Homo sapiens

<400> SEQUENCE: 1

```
gttcccaatc tgaagtgaag ccgagctggg cgagaagtag gggagggcgg tgctccgccg      60
cggtggcggt tgctatcgct tcgcagaacc tactcaggcag ccagctgag aagagttgag     120 ggaaagtgct gctgctggt ctgcagacgc gatggataac gtgcagccga aaataaaaca     180
tcgccccttc tgcttcagtg tgaaaggcca cgtgaagatg ctgcggctgg atattatcaa     240
ctcactggta acaacagtat tcatgctcat cgtatctgtg ttggcactga taccagaaac     300
cacaacattg acagttggtg gagggtgtt tgcacttgtg acagcagtat gctgtcttgc     360
cgacggggcc cttatttacc ggaagcttct gttcaatccc agcggtcctt accagaaaaa     420
gcctgtgcat gaaaaaaag aagttttgta atttatatt acttttagt ttgatactaa      480 gtattaaaca tatttctgta ttcttccaaa aaaaaaaaaa aaaaaaaaaa aaaa          534
```

<210> SEQ ID NO 2
<211> LENGTH: 99
<212> TYPE: PRT
<213> ORGANISM: Homo sapiens

<400> SEQUENCE: 2

```
Met Asp Asn Val Gln Pro Lys Ile Lys His Arg Pro Phe Cys Phe Ser
  1               5                  10                  15

Val Lys Gly His Val Lys Met Leu Arg Leu Asp Ile Ile Asn Ser Leu
                 20                  25                  30

Val Thr Thr Val Phe Met Leu Ile Val Ser Val Leu Ala Leu Ile Pro
             35                  40                  45

Glu Thr Thr Thr Leu Thr Val Gly Gly Gly Val Phe Ala Leu Val Thr
         50                  55                  60

Ala Val Cys Cys Leu Ala Asp Gly Ala Leu Ile Tyr Arg Lys Leu Leu
 65                  70                  75                  80
```

```
Phe Asn Pro Ser Gly Pro Tyr Gln Lys Lys Pro Val His Glu Lys Lys
            85                  90                  95

Glu Val Leu

<210> SEQ ID NO 3
<211> LENGTH: 459
<212> TYPE: DNA
<213> ORGANISM: Homo sapiens

<400> SEQUENCE: 3
atggataacg tgcagccgaa aataaaacat cgccccttct gcttcagtgt gaaaggccac      60
gtgaagatgc tgcggctggc actaactgtg acatctatga cctttttttat catcgcacaa    120 gcccctgaac catatattgt tatcactgga tttgaagtca ccgttatctt attttttcata   180 cttttatatg tactcagact tgatcgatta atgaagtggt tattttggcc tttgcttgat    240
attatcaact cactggtaac aacagtattc atgctcatcg tatctgtgtt ggcactgata    300 ccagaaaacca caacattgac agttggtgga ggggtgtttg cacttgtgac agcagtatgc    360
tgtcttgccg acgggcccct tatttaccgg aagcttctgt tcaatcccag cggtccttac    420
cagaaaaagc ctgtgcatga aaaaaagaa gttttgtaa                             459

<210> SEQ ID NO 4
<211> LENGTH: 152
<212> TYPE: PRT
<213> ORGANISM: Homo sapiens

<400> SEQUENCE: 4

Met Asp Asn Val Gln Pro Lys Ile Lys His Arg Pro Phe Cys Phe Ser
  1               5                  10                  15

Val Lys Gly His Val Lys Met Leu Arg Leu Ala Leu Thr Val Thr Ser
             20                  25                  30

Met Thr Phe Phe Ile Ile Ala Gln Ala Pro Glu Pro Tyr Ile Val Ile
         35                  40                  45

Thr Gly Phe Glu Val Thr Val Ile Leu Phe Phe Ile Leu Leu Tyr Val
     50                  55                  60

Leu Arg Leu Asp Arg Leu Met Lys Trp Leu Phe Trp Pro Leu Leu Asp
 65                  70                  75                  80

Ile Ile Asn Ser Leu Val Thr Thr Val Phe Met Leu Ile Val Ser Val
                 85                  90                  95

Leu Ala Leu Ile Pro Glu Thr Thr Thr Leu Thr Val Gly Gly Gly Val
            100                 105                 110

Phe Ala Leu Val Thr Ala Val Cys Cys Leu Ala Asp Gly Ala Leu Ile
        115                 120                 125

Tyr Arg Lys Leu Leu Phe Asn Pro Ser Gly Pro Tyr Gln Lys Lys Pro
    130                 135                 140

Val His Glu Lys Lys Glu Val Leu
145                 150

<210> SEQ ID NO 5
<211> LENGTH: 204
<212> TYPE: DNA
<213> ORGANISM: Homo sapiens

<400> SEQUENCE: 5
atggataacg tgcagccgaa aataaaacat cgccccttct gcttcagtgt gaaaggccac      60
gtgaagatgc tgcggctggt gttttgcactt gtgacagcag tatgctgtct tgccgacggg   120
```

```
gcccttattt accggaagct tctgttcaat cccagcggtc cttaccagaa aaagcctgtg      180
catgaaaaaa aagaagtttt gtaa                                             204
```

<210> SEQ ID NO 6
<211> LENGTH: 67
<212> TYPE: PRT
<213> ORGANISM: Homo sapiens

<400> SEQUENCE: 6

```
Met Asp Asn Val Gln Pro Lys Ile Lys His Arg Pro Phe Cys Phe Ser
 1               5                  10                  15

Val Lys Gly His Val Lys Met Leu Arg Leu Val Phe Ala Leu Val Thr
            20                  25                  30

Ala Val Cys Cys Leu Ala Asp Gly Ala Leu Ile Tyr Arg Lys Leu Leu
        35                  40                  45

Phe Asn Pro Ser Gly Pro Tyr Gln Lys Lys Pro Val His Glu Lys Lys
    50                  55                  60

Glu Val Leu
65
```

<210> SEQ ID NO 7
<211> LENGTH: 363
<212> TYPE: DNA
<213> ORGANISM: Homo sapiens

<400> SEQUENCE: 7

```
atggataacg tgcagccgaa aataaaacat cgccccttct gcttcagtgt gaaaggccac       60
gtgaagatgc tgcggctggc actaactgtg acatctatga ccttttttat catcgcacaa      120
gcccctgaac catatattgt tatcactgga tttgaagtca ccgttatctt attttttcata     180 cttttatatg tactcagact tgatcgatta atgaagtggt tattttggcc tttgcttgtg     240
tttgcacttg tgacagcagt atgctgtctt gccgacgggg cccttattta ccggaagctt     300
ctgttcaatc ccagcggtcc ttaccagaaa agcctgtgc atgaaaaaaa agaagttttg      360
taa                                                                    363
```

<210> SEQ ID NO 8
<211> LENGTH: 120
<212> TYPE: PRT
<213> ORGANISM: Homo sapiens

<400> SEQUENCE: 8

```
Met Asp Asn Val Gln Pro Lys Ile Lys His Arg Pro Phe Cys Phe Ser
 1               5                  10                  15

Val Lys Gly His Val Lys Met Leu Arg Leu Ala Leu Thr Val Thr Ser
            20                  25                  30

Met Thr Phe Phe Ile Ile Ala Gln Ala Pro Glu Pro Tyr Ile Val Ile
        35                  40                  45

Thr Gly Phe Glu Val Thr Val Ile Leu Phe Phe Ile Leu Leu Tyr Val
    50                  55                  60

Leu Arg Leu Asp Arg Leu Met Lys Trp Leu Phe Trp Pro Leu Leu Val
65                  70                  75                  80

Phe Ala Leu Val Thr Ala Val Cys Cys Leu Ala Asp Gly Ala Leu Ile
                85                  90                  95
```

```
-continued

Tyr Arg Lys Leu Leu Phe Asn Pro Ser Gly Pro Tyr Gln Lys Lys Pro
            100             105             110

Val His Glu Lys Lys Glu Val Leu
        115             120
```

NUCLEIC ACID MOLECULE ENCODING CHEMOKINE-LIKE FACTOR 1 (CKLF1)

This is a continuation-in-part of International Application PCT/CN00/00026, with an international filing date of Feb. 15, 2000, now abandoned.

1. FIELD OF THE INVENTION

The present invention provides chemokine-like factors (CKLFs) polypeptides with chemotactic and hematopoietic stimulating activities and polynucleotides encoding such polypeptides. Also provided is the method to produce such polynucleotides and polypeptides. The present invention further discloses a drug compound comprising a therapeutically effective amount of such CKLF polypeptides as well as pharmaceutically acceptable excipients and carriers. Also disclosed are the uses of such CKLF polypeptides and polynucleotides in diagnosis or treatment of immunodeficiency, hematopoietic diseases and primary tumors. The present invention also relates to the antibodies and antagonists of such CKLF polynucleotides.

2. BACKGROUND OF THE INVENTION

Cytokines are a superfamily of small proteins synthesized and secreted by different cells, which participate in the proliferation and differentiation of many kinds of cells and play essential roles in physiological and pathological processes. Cytokines include interleukins, colony stimulating factors, interferons, tumor necrosis factors, growth factors and chemokines. Many kinds of recombinant cytokines and their antagonists produced by using genetic engineering technology have been applied to clinical treatment and have enjoyed positive effects. This reflects the spacious applications of cytokines.

The superfamily of chemokine (also called chemotactic factor) comprises dozens of polypeptides with molecular weights of 8–12 KD. These polypeptides are similar in structure and in their chemotactic effects, and they play important roles in immune defense, immunoregulation, inflammation, hematopoietic regulation and vasculogenesis. The amino acid sequences of most of the chemokines share the same character of conserved four-cysteine (Cys) motif. According to the positions of the first and the second Cys, chemokines can be divided into four subfamilies named CXC, CC, $CX_3C$ and C, respectively, wherein C represents Cys and X represents any kind of amino acid. The members of CXC, such as IL-8, interferon-induced protein 10 (IFN-IP-10), and cytokine with melanocyte growth stimulating activity (MGSA) have their encoding genes usually located on chromosome 4 in human somatic cells, and activate and attract neutrophils and T lymphocytes. While the numbers of CC, such as macrophage inflammatory protein-1α (MIP-1α), macrophage inflammatory protein-1β(MIP-1β), monocyte chemoattractant protein-1(MCP-1) and cytokine regulated on activation, and normal T cell expressed and secreted (RANTES) have their encoding genes usually located on chromosome 17 in somatic cells, and mainly activate monocytes, lymphocytes, basophils and eosinophils. Fractalkine is the only identified member of the $CX_3C$ subfamily, which can activate and chemotacte T cells and monocytes. As for the C subfamily, only Lymphotactin (Ltn) is presently found, which can chemotacte lymphocytes.

The receptors of chemokines belong to the superfamily of GTP-binding protein which have the characteristic of seven transmembrane domains. In accordance with the specific combination to different numbers of chemokine subfamilies, chemokine receptors are named: CXC Receptor (CXCR), such as CXCR 1, CXCR 2, CXCR 3, and CXCR 4; CC Receptor (CCR), such as CCR 1, CCR 2, CCR 3, CCR 4, CCR 5, CCR 6 and CCR 7; $CX_3C$ Receptor ($CX_3CR$) (See Marco, B., et al., 1997, *Human Chemokines: An Update Annu. Rev. Immunol.* 15:675–705). Because chemokines play important roles in system immunization, inflammatory responses and hematopoietic regulation, some abnormal changes of chemokines or their receptors (e.g., the defect of chemokines or chemokine receptors, or the overexpression of chemokines, or the increase of soluble chemokine receptors) always result in some kind of infectious disease or autoimmune disease, or sometimes even in tumors. Therefore, the detection of chemokines or chemokine receptors can be used in clinical diagnosis to observe the development of diseases and to judge the curative effects. Recent studies show that HIV can invade the immune cells of human by combining with chemokine receptors, which indicate that chemokine receptors as well as chemokines are closely related to the infection and development of HIV disease. Hence, Chemokines could be used as promising drugs to block the invasion of HIV to immune cells (Cocchi, F., et al., 1995, "Identification of RANTES, MIP-1α, and MIP-1β as the Major HIV-Suppressive Factors Produced by $CD8^+$ T Cells," *Science* 270:1811). Furthermore, some chemokine drugs produced by bioengineering methods have been successively used in clinical tests and have the possibility to become useful medicines in the future. For instance, myeloid progenitor inhibitory factor-1 (MPIF-1) has been used as a protective hematopoietic drug in high-dose radiotherapy or chemotherapy for tumors (Marshall, A., 1998, "HGS launches "first" genomics product in clinic," *Nat. Biotechol.* 16:129).

The present invention is based on the finding that many types of cytokines or chemokines can be stimulated by phytohemagglutinin (PHA) (Brantschen, S., et al., 1989, "Differential expression of cytokine mRNAs cell lines," *Lymphokine Res* 8(3):163–72), while interleukin-10(IL-10) is a broad-spectrum inhibitor of cytokines (Di-Hwei, H., et al., 1990, *Science* 250:830). By using suppression subtractive hybridization (SSH) technique, some novel cytokines could be found. (Diatchenko, L., et al, 1996, "Suppression subtractive hybridization: A method for generating differentially regulated or tissue-specific cDNA probes and libraries," *Pro. Natl Acad. Sci. USA* 93:6025–30). Based on the above, the present inventors, by using SSH technique, identified and cloned CKLF1 gene from a cDNA library derived from U937 cell line, a human promonocytic cell line. Furthermore, the inventors disclose the biological activity and function of CKLF1 and its variants.

3. SUMMARY OF THE INVENTION

One aspect of the present invention relates to novel mature CKLF polypeptides which have chemotactic activities on immune cells and stimulatory effects on hematopoietic progenitor cells. Also provided are biologically active and diagnostically or therapeutically useful fragments, variants, analogs and derivatives thereof. The polypeptides of the present invention are of human origin.

Another aspect of the present invention relates to isolated nucleic acid molecules encoding polypeptides of the present invention, including mRNAs, cDNAs, genomic DNAs as well as variants, analogs, derivatives and biologically active and diagnostically or therapeutically useful fragments thereof.

Another aspect of the present invention relates to a method for producing such CKLF polypeptides by recombinant techniques comprising cloning nucleic acid sequences encoding the polypeptides of the present invention into suitable vectors, introducing recombinant vectors into prokaryotic and/or eukaryotic host cells by transduction, transfection or transformation methods, and culturing such prokaryotic and/or eukaryotic host cells under suitable conditions to express the CKLF polypeptides of the present invention.

Another aspect of the present invention relates to diagnostic or therapeutic uses of the CKLF polypeptides and polynucleotides in the treatment of immunodeficiency, hematopoietic diseases and primary tumors. It further relates to a method for diagnosing a disease or susceptibility to a disease comprising determining a mutation in the polynucleotide of the present invention. It still further relates to a method of diagnosis comprising analyzing for the presence of the polypeptide of the present invention.

Another aspect of the present invention relates to drug compounds comprising a therapeutically effective amount of such CKLF polypeptides or its functional fragments as well as pharmaceutically acceptable excipients and carriers. It further relates to a method for the treatment of a patient having need of CKLF comprising administering to said patient a therapeutically effective amount of the polypeptide.

Still another aspect of the present invention relates to polyclonal or monoclonal antibodies of the polypeptides of the present invention. It further relates to a method of using the antibody in the preparation of immunological adjuvants which can improve the curative effect of a DNA vaccine or a DNA drug.

Yet another aspect of the present invention relates to antagonists of the polypeptides of the present invention, which may be used to inhibit the action of such polypeptides, for example, in the treatment of rheumatoid arthritis, autoimmune diseases, tumors, and viral infections.

4. BRIEF DESCRIPTION OF DRAWINGS AND SEQUENCE LISTING

FIG. 1 depicts the process of isolating cDNAs from human U937 cells by suppression subtractive hybridization (SSH) techniques. Driver cDNA comes from U937 cells inhibited with IL-10. Tester cDNA comes from U937 cells stimulated with PHA.

FIGS. 5A–5I show the chemotactic activity of CKLF1 in different cells.

FIG. 5A shows the chemotactic effects of recombinant CKLF1 in the supernatants of eukaryotic cell culture to the DMSO stimulated HL-60 cells.

FIG. 5B shows the chemotactic effects of recombinant CKLF1 in the supernatants of eukaryotic cell culture to mouse celiac macrophages.

FIG. 5C shows the chemotactic effects of recombinant CKLF1 in the supernatants of eukaryotic cell culture to mouse lymphocytes.

FIG. 5D shows the chemotactic effects of recombinant CKLF1 in the supernatants of eukaryotic cell culture to human PBMC.

FIG. 5E shows the chemotactic effects of recombinant CKLF 1 in the supernatants of eukaryotic cell culture to human neutrophils.

FIG. 5F shows the chemotactic effects of recombinant CKLF 1 in the supernatants of eukaryotic cell culture to U937 cells.

FIG. 5G shows the chemotactic effects of recombinant CKLF1 in the supernatants of eukaryotic cell culture to K562 cells.

FIGS. 5H and 5I show the chemotactic effects of recombinant CKLF1 in the supernatants of eukaryotic cell culture to mouse celiac macrophages and lymphocytes, respectively.

Figure 8A:
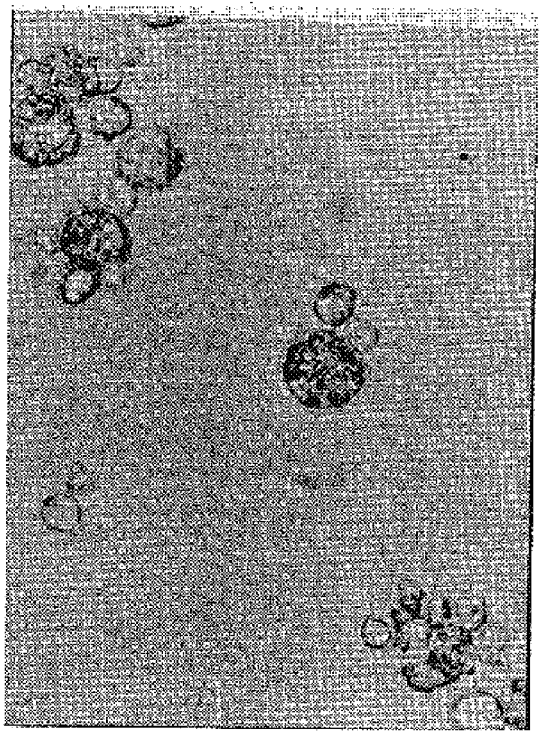
Figure 8B:
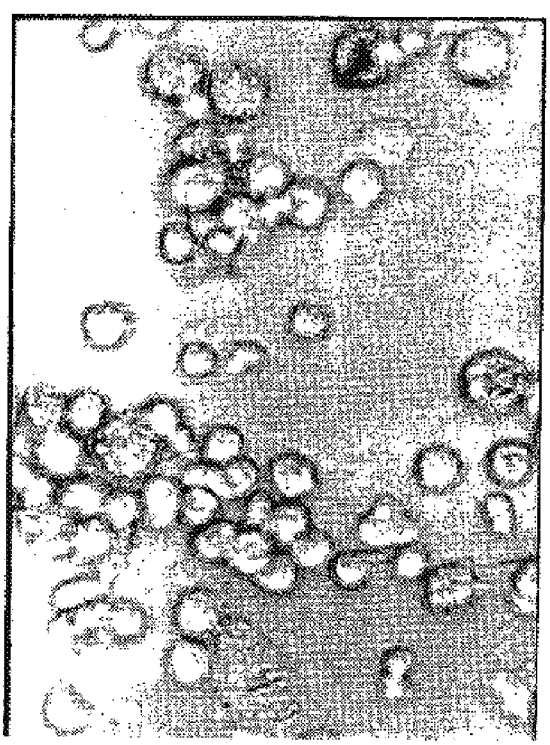

FIGS. 8A and 8B show the morphologic changes of mouse bone marrow cells after stimulation with CKLF1. FIG. 8A shows the result of the pCDI control group. FIG. 8B shows the result of the pCDI-CKLF1 group.

Figure 9:
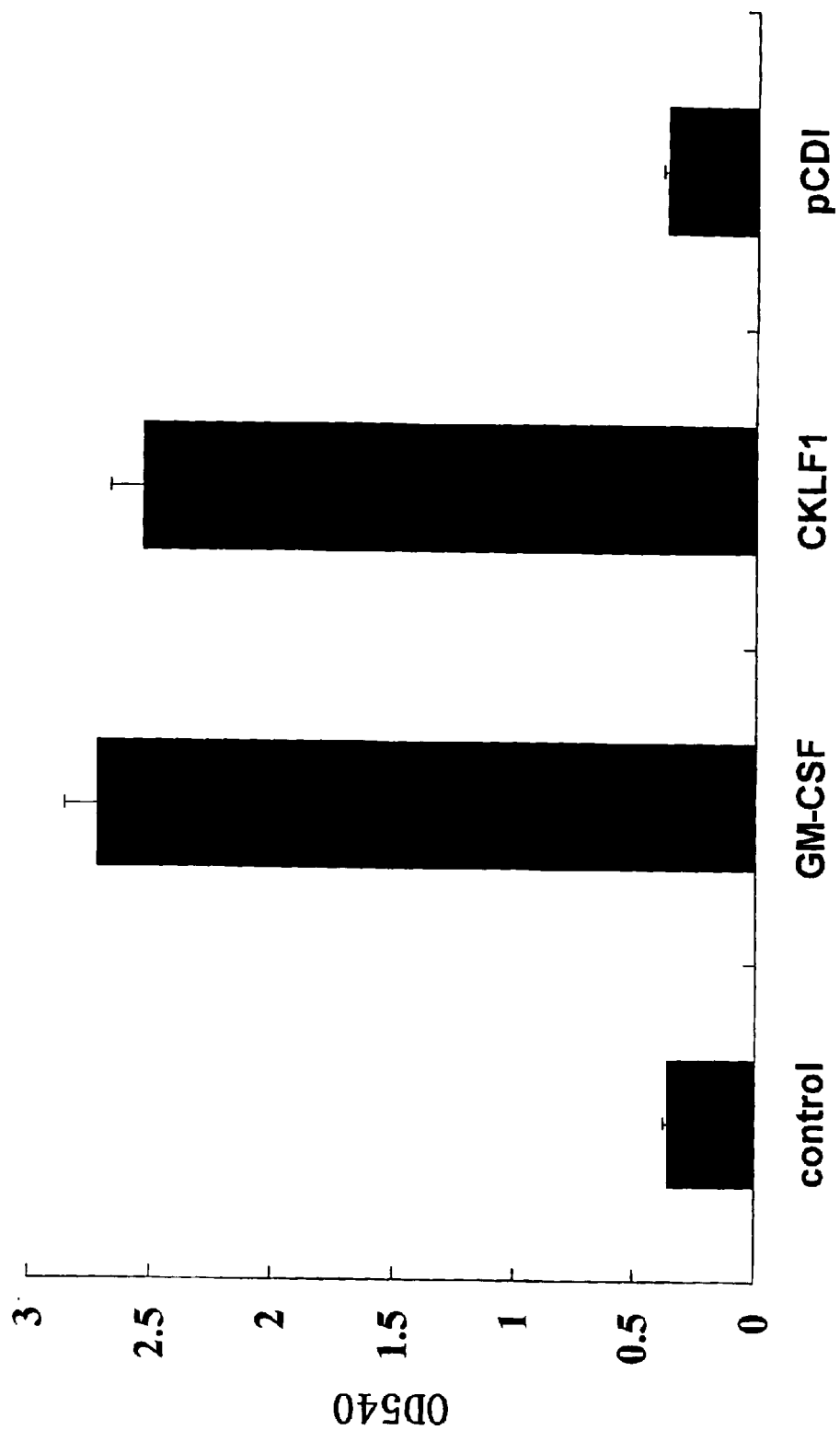

FIG. 9 depicts the result of the MTT test, showing the enhancing effect of recombinant CKLF1 to the proliferation of human bone marrow cells.

Figure 10:
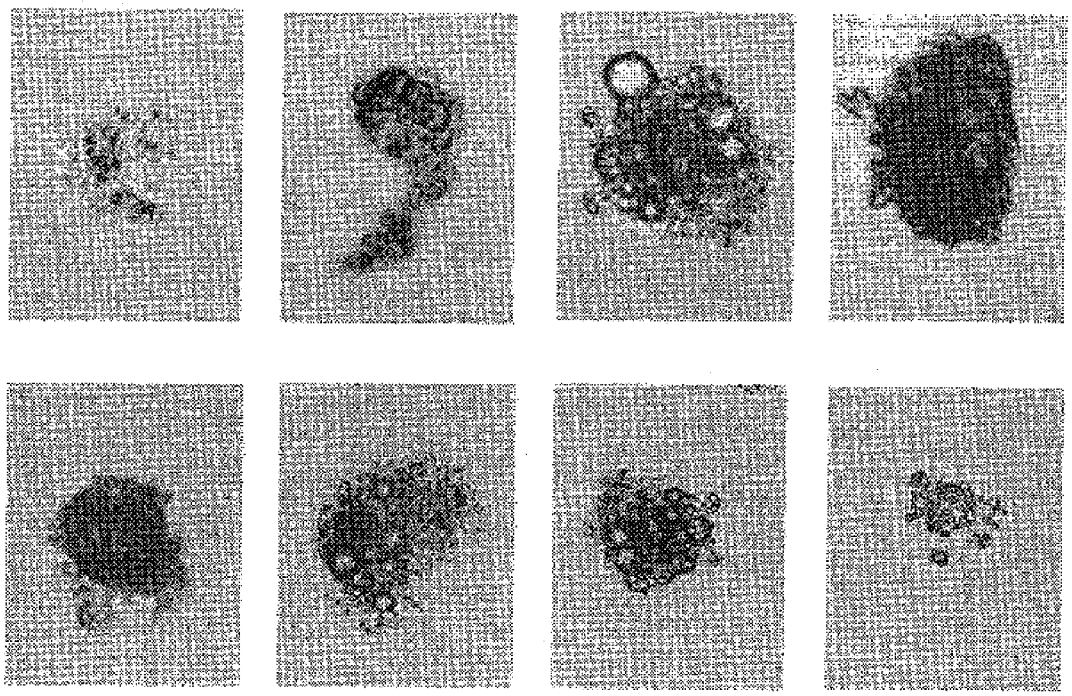

FIG. 10 shows the colonial morphology of human bone marrow cells after stimulation with CKLF 1 (incubated for 20 days).

Figure 11A:
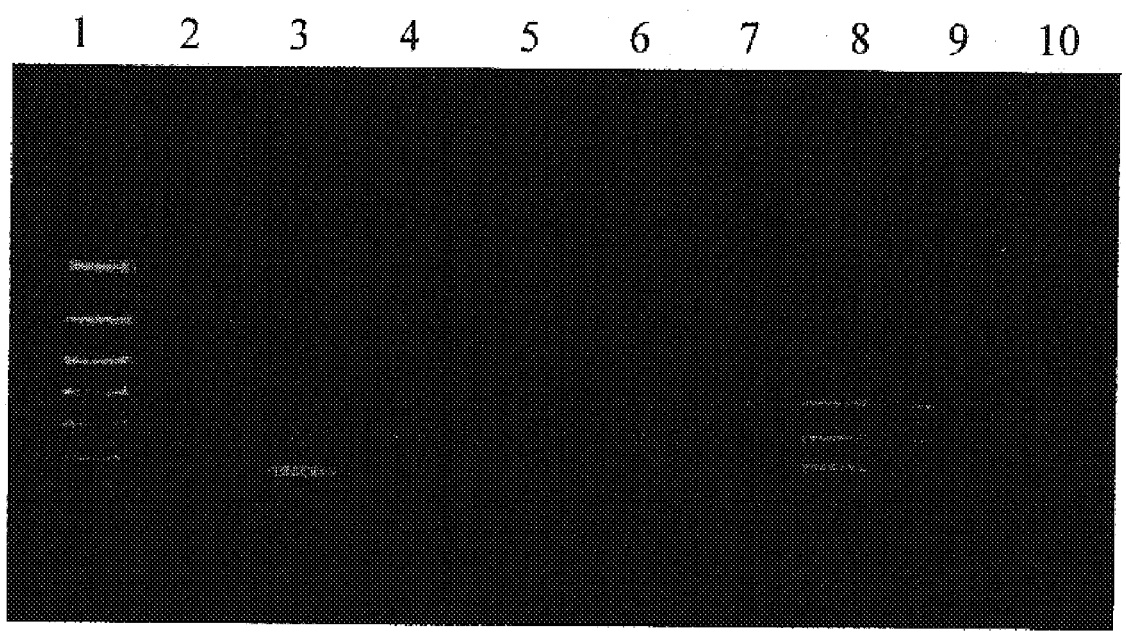
Figure 11B:
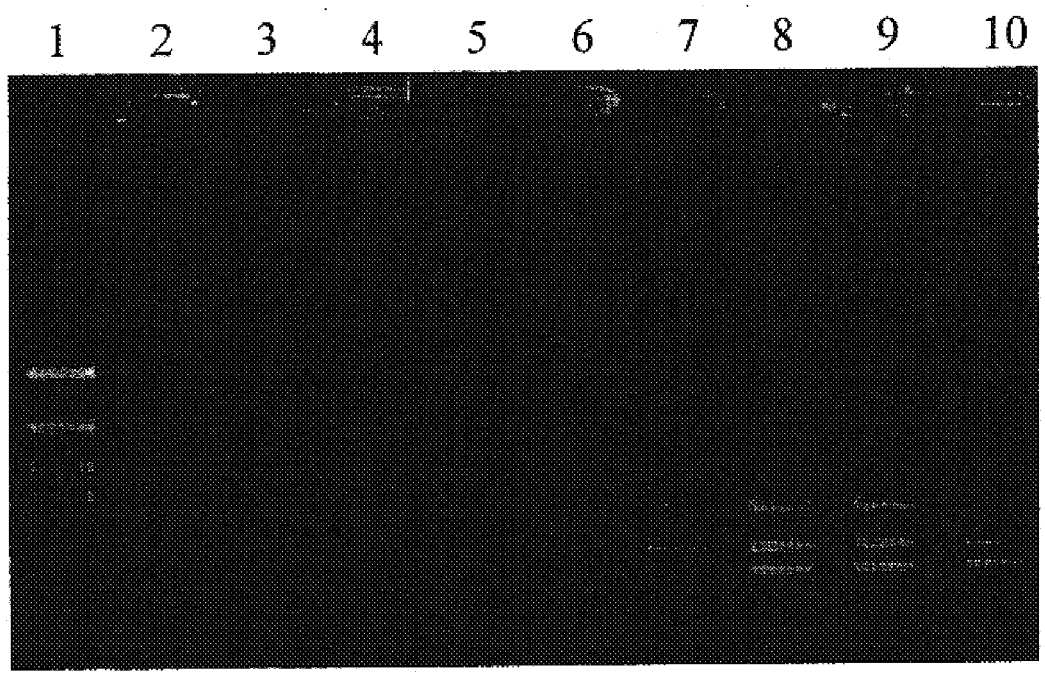
Figure 11C:
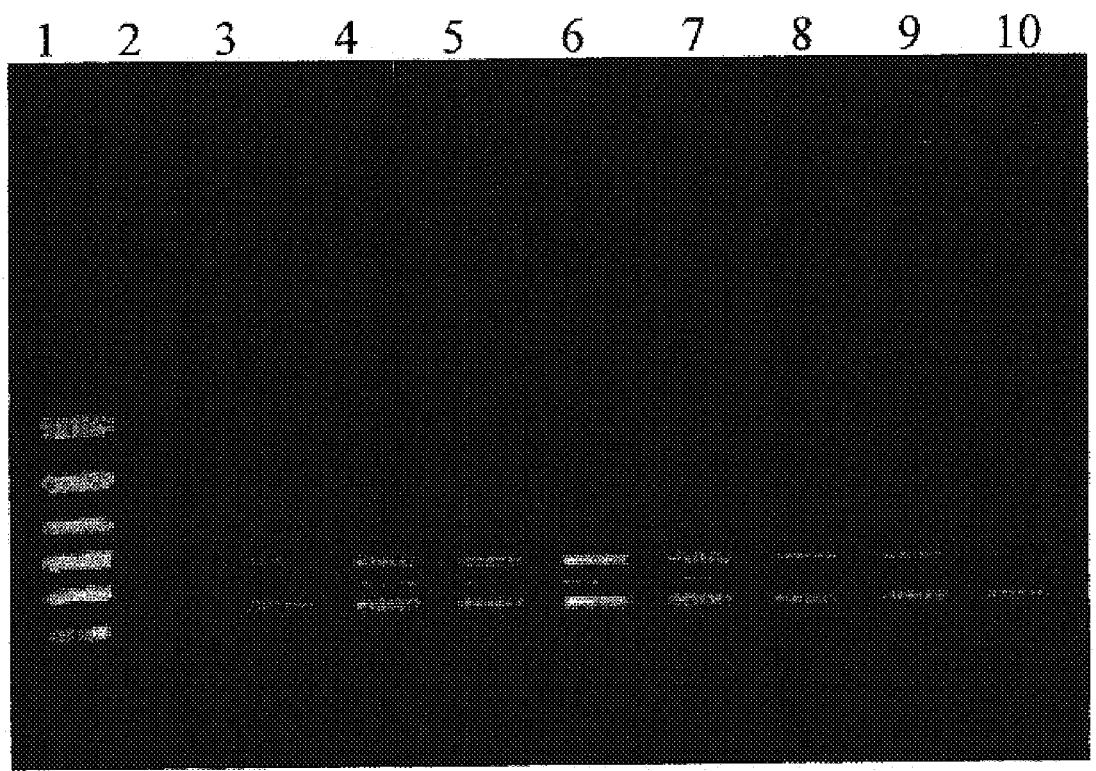
Figure 11D:
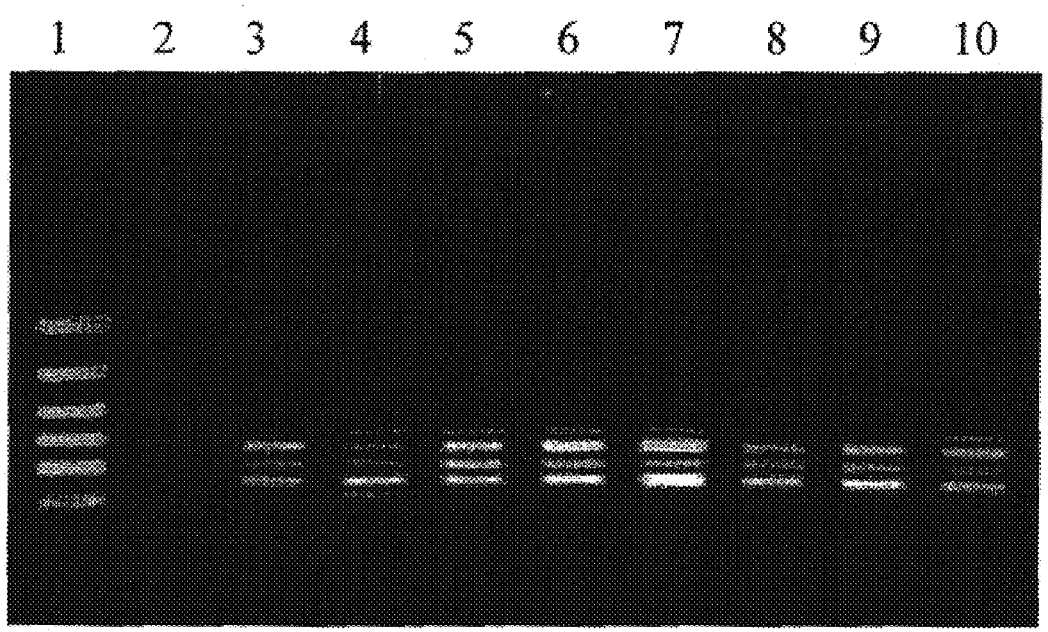

FIGS. 11A and 11B show the expression of CKLF1 and its variants in normal adult tissues. FIGS. 11C and 11D display the expression of CKLF1 and its variants in fetal tissues and a wide variety of tumor tissues.

Figure 12A:
Figure 12B:
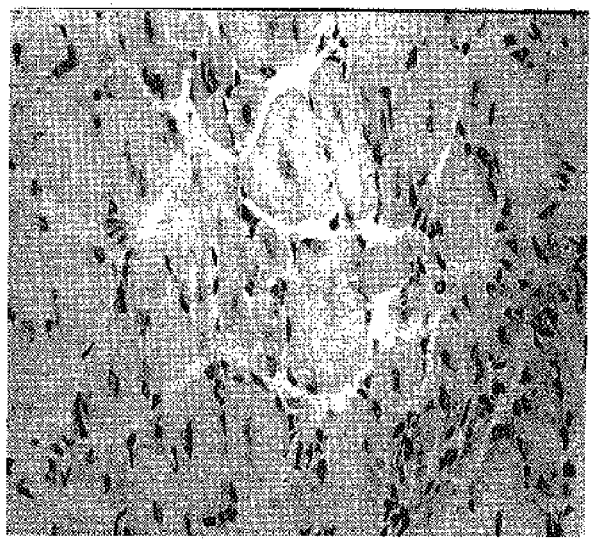

FIGS. 12A and 12B show the change of cross-sections of anterior tibial muscle of BALB/c mice after direct injection of pCDI and pCDI-CKLF1 plasmids. Cross-sections were stained with acid phosphatase (ACP) and hematoxylin-eoxin (HE) 10 days after injection. FIG. 12A shows the result of the pCDI control group, while FIG. 12B shows the result of the pCDI-CKLF1 group, in which muscle fiber regeneration was evidently observed. (Original magnification: 40×)

Figure 13A:
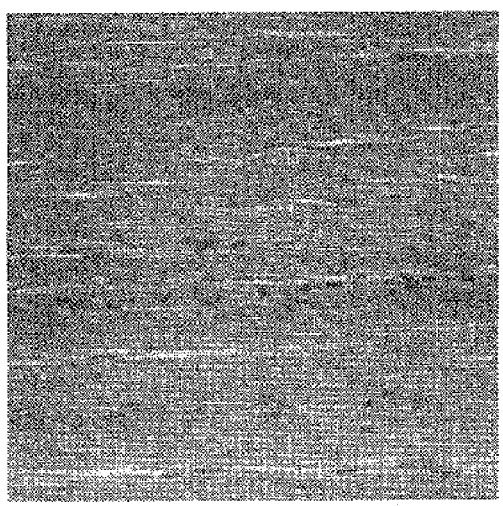
Figure 13B:

FIGS. 13A and 13B show the change of anterior tibial muscle vertical-sections of BALB/c mice after directly injection of pCDI and pCDI-CKLF1 plasmids. Vertical-sections were stained with HE 10 days after injection. FIG. 13A shows the result of the pCDI control group, while FIG. 13B shows the result of the pCDI-CKLF1 group, in which muscle fiber regeneration was evidently observed. (Original magnification: 40×)

SEQ ID NO: 1 displays the polynucleotide of CKLF1, including the open reading frame of CKLF1 cDNA.

SEQ ID NO: 2 displays the amino acid sequence of CKLF 1 deduced from SEQ ID NO: 1.

SEQ ID NO: 3 displays the polynucleotide of CKLF2.

SEQ ID NO: 4 displays the amino acid sequence of CKLF2 deduced from SEQ ID NO: 3.

SEQ ID NO: 5 displays the polynucleotide of CKLF3.

SEQ ID NO: 6 displays the amino acid sequence of CKLF3 deduced from SEQ ID NO: 5.

SEQ ID NO: 7 displays the polynucleotide of CKLF4.

SEQ ID NO: 8 displays the amino acid sequence of CKLF4 deduced from SEQ ID NO: 7.

5. DETAILED DESCRIPTION OF THE INVENTION

One aspect of the present invention relates to an isolated nucleic acid (polynucleotide) which encodes for the mature polypeptide having the deduced amino acid sequence selected from the group consisting of SEQ ID NO:2, SEQ ID NO:4, SEQ ID NO:6, SEQ ID NO:8, and the mature polypeptide encoded by the cDNA of the clone deposited as CGMCC NO.0392. It also relates to naturally occurring variants of these polynucleotides. It further relates to a polynucleotide capable of hybridizing to the polynucleotide encoding the polypeptide as set forth in SEQ ID NO:2 or the polynucleotide encoding the mature polypeptide having the amino acid sequence expressed by the cDNA contained in CGMCC Deposit No.0392. It still further relates to a polynucleotide which is at least 85% identical to the polynucleotide encoding the polypeptide as set forth in SEQ ID NO:2 or the polynucleotide encoding the mature polypeptide having the amino acid sequence expressed by the cDNA contained in CGMCC Deposit No.0392.

The polynucleotide encoding the CKLF1 polypeptide of the present invention was discovered in a cDNA library derived from a human promonocytic cell line U937. As shown in SEQ ID NO: 1, The full length cDNA of CKLF 1 polynucleotide includes 534 base pairs including a "ATTAAA" polyadenylation signal and a polyadenylic acid (poly(A)) tail. The open reading frame encoding a protein of 99 amino acid residues is from nucleotide 152 to nucleotide 448. The CKLF1 protein contains two successive cysteine residues found in all the members of the CC subfamily, but exhibits little homology to known proteins. The polynucleotide of CKLF1 shares no obvious homology with known polynucleotides and its GeneBank access number is AF096895.

The polynucleotides encoding the CKLF2, CKLF3 and CKLF4 polypeptides are shown in SEQ ID NO:3, SEQ ID NO:5 and SEQ ID NO:7, respectively. There is no frame shift mutation in the sequences of SEQ ID NO:3, SEQ ID NO:5 and SEQ ID NO:7 compared with that of SEQ ID NO: 1. The deduced mature polypeptides of CKLF2, CKLF3 and CKLF 4 have 152, 67 and 120 amino acids, respectively. It has been assumed that the polynucleotides of CKLF2, CKLF3 and CKLF4 are formed by different splicing of the CKLF1 gene during the post-transcription course. The CKLF2, CKLF3 and CKLF4 polypeptides are probably allelic gene variants of the CKLF1 polypeptide (SEQ ID NO:2). The access numbers of CKLF2, CKLF3 and CKLF4 in GeneBank are AF135380, AF135381, and AF145216, respectively.

The polynucleotide of the present invention may be in the form of RNA or in the form of DNA, which DNA includes cDNA, genomic DNA, and synthetic DNA. The DNA may be double-stranded or single-stranded, and if single stranded it may be the coding strand or non-coding (anti-sense) strand. The coding sequence which encodes the mature polypeptide selected from the group consisting of SEQ ID NO:2, SEQ ID NO:4, SEQ ID NO:6 and SEQ ID NO:8 may be identical to the coding sequence shown in SEQ ID NO: 1, SEQ ID NO:3, SEQ ID NO:5 or SEQ ID NO:7 or that of the deposited clone CGMCC NO. 0392 or may be a different coding sequence which coding sequence, as a result of the redundancy or degeneracy of the genetic code, encodes the same mature polypeptide as the DNA of SEQ ID NO:1, SEQ ID NO:3, SEQ ID NO:5 or SEQ ID NO:7 or the deposited cDNA.

The polynucleotide which encodes for the mature polypeptide selected from the group consisting of SEQ ID NO:2, SEQ ID NO:4, SEQ ID NO:6 and SEQ ID NO:8, or for the mature polypeptide encoded by the deposited cDNA may include, but is not limited to: (i) the coding sequence for the mature polypeptide; (ii) the coding sequence for the mature polypeptide and an additional coding sequence such as a leader or secretory sequence or a proprotein sequence; and (iii) the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence selected from the group consisting of SEQ ID NO:2, SEQ ID NO:4, SEQ ID NO:6, SEQ ID NO:8 or the polypeptide encoded by the cDNA of the deposited clone. The variant of the polynucleotides may be a naturally occurring allelic variant of the polynucleotide or a non-naturally occurring variant of the polynucleotide.

Thus, the present invention includes polynucleotides encoding the same mature polypeptide as shown in SEQ ID NO:2, SEQ ID NO:4, SEQ ID NO:6, SEQ ID NO:8 or the same mature polypeptide encoded by the cDNA of the deposited clone as well as variants of such polynucleotides which variants encode for a fragment, derivative or analog of the polypeptide of SEQ ID NO:2, SEQ ID NO:4, SEQ ID NO:6, SEQ ID NO:8, or the polypeptide encoded by the cDNA of the deposited clone. Such nucleotide variants include deletion variants, substitution variants and addition or insertion variants.

As indicated above, the polynucleotide may have a coding sequence which is a naturally occurring allelic variant of the coding sequence shown in SEQ ID NO:2, SEQ ID NO:4, SEQ ID NO:6, SEQ ID NO:8 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotide may also encode for a proprotein which is the mature protein plus additional 5' amino acid residues. A mature protein having a prosequence is a proprotein and is an inactive form of the protein. Once the prosequence is cleaved, an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g., COS-7 cells, is used. The HA tag corresponds to an epitope derived from the influenza hemagglutinin protein.

The term "gene" means the segment of DNA involved in producing a polypeptide chain; it includes regions preceding and following the coding region (leader and trailer) as well as intervening sequences (introns) between individual coding segments (exons).

Fragments of the full length CKLFs gene may be used as a hybridization probe for a cDNA library to isolate the full length CKLFs gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete CKLF gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the above-described CKLF1 sequence if there is at least 85%, preferably at least 90%, and more preferably at least 95% identity between the sequences. The present invention particularly relates to polynucleotides which hybridize under stringent conditions to the above-described CKLF1 polynucleotide. In this context, stringent heterologous hybridization conditions are as follows: hybridization at 55–64° in 0.25M sodium phosphate (pH7.2), 1 mM EDTA 0.5% blocking reagent, 5% SDS, 50 μg/ml denatured herring sperm DNA and 20 ng/ml denatured probe for 18–24 hours followed by two 10 minutes washes in 125 mM sodium phosphate (pH7.2), 0.05 mM EDTA, 2.5% SDS at 55–64° and two 10 minutes washes in 25 mM sodium phosphate (pH7.2), 0.01 mM EDTA, 0.5% SDS at room temperature. The more stringent heterologous hybridization conditions are described as follows: hybridization at 65° in 0.25M sodium phosphate (pH 7.2), 1 mM EDTA 0.5% blocking reagent, 5% SDS, 50 μg/ml denatured herring sperm DNA and 20 ng/ml denatured probe for 18–24 hours followed by two 10 minutes washed in 125 mM sodium phosphate (pH7.2), 0.05 mM EDTA, 2.5% SDS at 65° and two 10 minutes washes in 25 mM sodium phosphate (pH7.2), 0.01 mM EDTA,0.5% SDS at room temperature. The polynucleotides which hybridize to the above-described CKLF1 polynucleotide in a preferred embodiment encode polypeptides which either retain substantially the same biological function or activity as the mature polypeptide encoded by the cDNAs of SEQ ID NO:1 or the deposited cDNA(s).

Alternatively, the polynucleotide may have at least 20 bases, preferably 30 bases, and more preferably at least 50 bases which hybridize to the CKLF1 polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 85% identity, preferably at least 90% and more preferably at least a 95% identity to a CKLF1 polynucleotide which encodes the polypeptide of SEQ ID NO:2 as well as fragments thereof, which fragments have at least 30 bases and preferably at least 50 bases and to polypeptides encoded by such polynucleotide.

The deposits(s) referred to herein will be maintained at the China Committee For Culture Collection of Microorganisms, General Microbiological Culture Center, Zhongguancun, Beijing, China 100080 (Name and Address of Depository) under the terms of the Budapest Treaty on the International Recognition of the Deposit of Microorganisms for purposes of Patent Procedure. These deposits are "provided" merely as a convenience to those skill in the art and are not an admission that a deposit is required under 35 U.S.C. §112. The sequence of the polynucleotides contained in the deposited materials, as well as reference and are controlling in the event of any conflict with any description of sequences herein. A license may be required to make, use or sell the deposited materials, and no such license is hereby granted.

Another aspect of the present invention relates to a CKLF polypeptide which has the deduced amino acid sequence selected from the group consisting of SEQ ID NO:2, SEQ ID NO:4, SEQ ID NO:6, SEQ ID NO:8, the amino acid sequence encoded by the cDNA of CGMCC Deposit NO.0392, and fragments, analogs and derivatives of such polypeptide. The CKLF polypeptides have chemotactic activities on immune cells and stimulatory effects on hematopoietic progenitor cells. Chemokine-like factors were originally called U937-derived chemokines (UCKs). Later, in accordance with the suggestion raised by International Committee on Standardized Genetic Nomenclature, UCKs were named chemokine-like factors (CKLFs).

The CKLF1 has the deduced amino acid sequence as set forth in SEQ ID NO:1 or has the amino acid sequence encoded by the deposited clone CGMCC NO.0392. CKLF1 is composed of 99 amino acid residues with the molecular weight of 10,923 Dalton. The analysis of the amino acid sequence shows CKLF1 has the obvious structural characteristics of the CC chemokine subfamily, which contains three cysteine residues, the last two of which are organized in a pattern typical of the CC chemokine subfamily. The deduced CKLF1 polypeptide has no typical signal cleavage site and no putative N-glycosylation site. It is found that CKLF1 has 46% homology with permease of *Caenorhabditis elegans* at residue 35 through residue 79 and shares no obvious homology with other proteins. CKLF1 belongs to secretory protein, which can be detected in human colon, pancreas, brain, heart, embryonic tissue and the related tumors. The experiments reveal that CKLF1 has obvious chemotactic activity and can remarkably promote the proliferation of hematopoietic cells and skeletal cells. (See Examples 6, 7, 8 and 10)

CKLF2, CKLF3 and CKLF4 have deduced amino acid sequences as described in SEQ ID NO: 4, SEQ ID NO: 6 and SEQ ID NO: 8. The polypeptides of CKLF2, CKLF3 and CKLF 4 have 152, 67 and 120 amino acids, respectively. CKLF 2, 3,and 4 can be detected in many kinds of tumor tissues such as carcinoma of colon, adenocarcinoma of lung, prostatic carcinoma and oophoroma and embryonic tissue. The expression level of CKLF2 is much higher in many types of primary tumor cells and embryonic cells than in the normal cells.

The terms "fragment", "derivative" and "analog" when referring to the polypeptide of CKLFs (SEQ ID NO:2, SEQ ID NO:4, SEQ ID NO:6 or SEQ ID NO:8 or that encoded by the deposited cDNA) means a polypeptide which retains essentially the same biological function or activity as such polypeptides. Thus, an analog includes a protein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of CKLF (SEQ ID NO:2, SEQ ID NO:4, SEQ ID NO:6 or SEQ ID NO:8) or that encoded by the deposited cDNA may be: (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence that is employed for purification of the mature polypeptide or a proprotein sequence; or (v) splice variants of the mature polypeptide which are lacking certain amino acid residues yet still retain biological activity. Such fragments, derivatives or analogs are deemed to be within the scope of those skilled in the art from the teaching herein. The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally occurring polypeptide and polynucleotide present in a living animal is not isolated, but the same polypeptide or polynucleotide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2, SEQ ID NO:4, SEQ ID NO:6 and SEQ ID NO:8 (in particular the mature polypeptide) as well as polypeptides which have at least 85% similarity (preferably a 85% identity) to the polypeptide of SEQ ID NO: 2, and more preferably at least 90% similarity (more preferably a 90% identity) to the polypeptide of SEQ ID NO: 2, and still more preferably at least 95% similarity (still more preferably a 95% identity) to the polypeptide of SEQ ID NO: 2 and also include portions of such polypeptides with such portion of the polypeptide generally containing at least 30 amino acids and more preferably at least 50 amino acids.

As known in the art, "similarity" between two polypeptides is determined by comparing the amino acid sequence and the conserved amino acid substitutes of one polypeptide to the sequence of a second polypeptide.

Fragments or portions of the polypeptides of the present invention may be employed for producing the corresponding full-length polypeptide by peptide synthesis. Therefore, the fragments may be employed as intermediates for producing the full-length polypeptides. Fragments or portions of the polypeptides of the present invention may be used to synthesize full-length polynucleotides of the present invention. Depending upon the host employed in a recombinant production procedure, the polypeptides of the present invention may be glycosylated or may be non-glycosylated. Polypeptides of the invention may also include an initial methionine amino acid residue.

Another aspect of the present invention relates to vectors which include polynucleotides of the present invention, host cells which are genetically engineered with vectors of the invention and the production of the polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polynucleotides by recombinant techniques. Thus, for example, the polynucleotide may be included in any one of a variety of expression vectors for expressing a polypeptide. Such vectors include chromosomal, nonchromosomal and synthetic DNA sequences (e.g., derivatives of SV40, bacterial plasmids, phage DNA, baculovirus, yeast plasmids, vectors derived from combinations of plasmids and phage DNA, and viral DNA such as vaccina, adenovirus, fowl pox virus, and pseudorabies). However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. Examples of such promoters are: LTR or SV40 promoter, the $E.$ $coli.$ lac or trp, the phage lambda promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

Representative examples of appropriate hosts are: (i) bacterial cells, such as $E.$ $coli,$ Streptomyces, *Salmonella typhimurium*, (ii) fungal cells, such as yeast, (iii) insect cells, such as Drosophila S2 and SDodoptera Sf9, (iv) animal cells, such as CHO, COS, TF-1, U937 and Hela, (v) adenoviruses, (vi) plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: Bacterial: pQE70, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pMT-hIL3 (Ma Dalong et al., 1991, *High-tech Communication* 11:26–29), pQE-9 (Qiagen), pD10 and Pnh18A (Stratagene), pKK233-3, pDR540 and pRIT5 (Pharmacia), pcDNA3 (Invitrogen), pCI (Promega), pWL-NEO and pSG (Stratagene) and pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Examples of named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described in Sambrook et al., 1989, *Molecular Cloning: A Laboratory Manual*, Second Edition, Cold Spring Harbor, N.Y.

Transcription of the DNA encoding the polypeptides of the present invention by higher eukaryotes is increased by inserting an enhancer sequence into the vector. Enhancers are cis-acting elements of DNA, usually from about 10 to 300 bp, that act on a promoter to increase its transcription. Examples include the SV40 enhancer on the late side of the replication origin 100 to 270 bp, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRPI gene, and a promoter derived from a highly-expressed gene to direct transcription of a downstream structural sequence. Such promoters can be derived from operons encoding glycolytic enzymes such as 3-phosphoglycerate kinase (PGK), acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC37017). Such commercial vectors include, for example, KK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can also be employed to express recombinant protein. Examples of mammalian expression systems include the COS-7 lines of monkey kidney fibroblasts and other cell lines capable of expressing a compatible vector, for example, the CHO, Hela and BHK cell lines. Mammalian expression vectors will comprise an origin of replication, a suitable promoter and enhancer, and any necessary ribosomal binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography, etc.

Still another aspect of the present invention relates to uses of the CKLF1 polypeptide and its coding polynucleotide in the diagnosis and treatment of some diseases. First, the CKLF1 polypeptide has a broad-spectrum chemotaxis to many kinds of cells (see Example 6), which implies it can be used to treat some infectious diseases. For example, the chemotactic activity of the CKLF1 polypeptide to inflammatory cells may be used in the preparation of anti-inflammatory drugs containing the CKLF1 polypeptide or its functional fragments to cure autoimmune diseases. Second, the CKLF1 polypeptide has the capability of promoting the proliferation and colony formation of bone marrow cells, as described in Examples 7 and 8. Thereby, it can be used to stimulate the hematopoietic function of the body and to treat hematopoietic system diseases, including primary and secondary hematopoietic disorders. Third, the CKLF1 polypeptide has the capability of promoting cell proliferation. As shown in Example 10, the CKLF 1 polypeptide can stimulate the proliferation of skeletal cells and hair follicles in vivo, which implies it can be used to treat myophagism or other degenerative diseases. It has been found that in the process of proliferation, skeletal cells are more prone to accept exogenous DNA, therefore, to promote the absorption of DNA vaccines or drugs, CKLF1 can be concurrently administrated or injected with DNA vaccines or drugs to improve the immunocompetency of the body and to improve the curative effect. Furthermore, the CKLF1 polypeptide of the present invention can promote the proliferation of hair follicular cells and can be used as a follicular proliferation agent to cure baldness. Fourth, the CKLF1 polynucleotide can be expressed in many tissues and cells, especially in some tumor cells (see Example 9), which implies that the CKLF1 polynucleotide can be used as a diagnostic reagent to detect the abnormal CKLF1 gene level in some cells.

Detection of a mutated form of the gene of the present invention will allow a diagnosis of a disease or a susceptibility to a disease which results from an under-expression of the polypeptide of the genetic testing based on the DNA sequence. Differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different fragments are retarded in the gel at different positions according to their specific melting or partial melting temperatures. Sequence changes at specific locations may also be revealed by nuclease protection assays, such as RNase and S1 protection or the chemical cleavage method.

Thus, the detection of a specific DNA sequence may be achieved by methods such as hybridization, RNase protection, chemical cleavage, direct DNA sequencing or the use of restriction enzymes (e.g., Restriction Fragment Length Polymorphisms (RFLP) and Southern blotting of genomic DNA).

In addition to more conventional gel-electrophoresis and DNA sequencing, mutations can also be detected by in situ analysis.

The present invention also relates to diagnostic assays for detecting altered levels of the polypeptide of the present invention in various tissues since an over-expression of the proteins compared to normal control tissue samples can detect the presence of certain disease conditions such as some primary tumors. Assays used to detect levels of the polypeptide of the present invention in a sample derived from a host are well-known to those of skill in the art and include radioimmunoassays, competitive-binding assays, Western Blot analysis, and preferably an ELISA assay. An ELISA assay initially comprises preparing an antibody specific to an antigen of the polypeptide of the present invention, preferably a monoclonal antibody. In addition, a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g., a polystyrene dish that binds the proteins in the sample. Any free protein binding sites on the dish are then covered by incubating with a non-specific protein such as bovine serum albumin. Next, the monoclonal antibody is incubated in the dish during which time the monoclonal antibodies attach to any polypeptides of the present invention attached to the polystyrene dish. All unbound monoclonal antibodies are washed out with a buffer. The reporter antibody linked to horseradish peroxidase is now placed in the dish resulting in the binding of the reporter antibody to any monoclonal antibody bound to the polypeptides of the present invention. The unattached reporter antibody is then washed out. Peroxidase substrates are added to the dish and the amount of color developed in a given time period is a measurement of the amount of protein present in a given volume of patient sample when compared against a standard curve.

A competition assay may also be employed to determine levels of the polypeptide of the present invention in a sample derived from the hosts. Such an assay comprises isolating plasma membranes which over-express the receptor for the polypeptide of the present invention. A test sample containing the polypeptides of the present invention which have been labeled, are then added to the plasma membranes and incubated for a set period of time. Also added to the reaction mixture is a sample derived from a host which is suspected of containing the polypeptide of the present invention. The reaction mixtures are passed through a filter which is rapidly washed and the bound radioactivity is then measured to determine the amount of competition for the receptors and therefore the amount of the polypeptides of the present invention in the sample.

The sequences of the present invention are also valuable for chromosomal identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used include in situ hybridization, prescreening with labeled flow-sorted chromosomes and preselection by hybridization to construct chromosome-specific cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases.

Once a sequence has been mapped to a precise chromosomal location, the physical position of the sequence on the chromosome can be correlated with genetic map data. Such data are found, for example, in V. McKusick, "Mendelian Inheritance in Man" (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences between the cDNA or genomic sequences of affected and unaffected individuals. If a mutation is observed in some or all of the affected individuals but not in any normal individuals, then the mutation is likely to be the causative agent of the disease.

Still further, another aspect of the present invention relates to employing the polypeptide of the present invention in combination with a suitable pharmaceutical carrier or excipient to make drug compounds. Such drug compounds comprise a therapeutically effective amount of the polypeptide or compound, and a pharmaceutically acceptable carrier or excipient. The formulation should suit the mode of administration. Such a carrier includes but is not limited to saline, dextrose, buffered saline, glycerol, water, ethanol and combinations thereof. Furthermore, accessory ingredients or additives may be added to such drug compounds, for example, reagents capable of cooperative with CKLF1; protein protection reagents such as the human serum protein, the low-molecular weight peptide, glycine or lysine; the metallic positive ions such as $Zn^{2+}$, $Mn^{2+}$, $Mg^{2+}$ and $Ca^{2}$; stabilizers such as polyethylene glycol, methylol cellulose, polyglycine, glutathione; proteinase inhibitors and free radical cleaning reagents such as superoxide dismutase (SOD), Vitamin E, Vitamin C, and skin penetrating reagents like dimethyl sulfoxide DMSO.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or compounds of the present invention may be employed in conjunction with other therapeutic compounds.

The pharmaceutical compositions may be administered in a convenient manner such as by oral, topical, intravenous, intraperitoneal, intramuscular, subcutaneous, intranasal or intradermal routes. The pharmaceutical compositions are administered in an amount which is effective for treating and/or prophylaxis of the specific indication.

Yet another aspect of the present invention relates to antibodies specific to the CKLF1 polypeptide. The CKLF1 polypeptide, its functional fragments, or other derivatives or analogs thereof, can be used as immunogens to produce antibodies thereto. These antibodies can be, for example, polyclonal or monoclonal antibodies. The present invention also includes chimeric, single chain and humanized antibodies, as well as antibody-binding fragments (Fab), or that of a Fab expression library. Various procedures known in the art may be used for the production of such antibodies and fragments. For preparation of monoclonal antibodies, any technique that provides antibodies produced by continuous cell line cultures can be used. The EBV-hybridoma technique may be used to produce human monoclonal antibodies. Also, transgenic mice may be used to express humanized antibodies to immunogenic polypeptide products of this invention. Antibodies corresponding to the CKLF1 polypeptide can be generated by directly injecting the CKLF1 polypeptide into an animal or by administering the polypeptide to an animal, preferably a non-human animal. Antibodies can be used to isolate the polypeptide from tissue expressing the CKLF1 polypeptide. Even antibodies to a fragment of the CKLF1 polypeptide can be used to isolate the whole native CKLF1 polypeptide.

Still another aspect of the present invention relates to antagonists of the CKLF1 polypeptide which can block or inhibit the activity of the CKLF1 polypeptide. Such antagonists may be employed to prepare a drug compound by combining with one or more pharmaceutically acceptable carrier(s) or excipient(s). By use as vaccines and introduced into tumor cells, the antagonists of the present invention may play a significant role in the treatment of tumors. It is also possible to use antagonists of the present invention to treat autoimmune diseases such as rheumatoid arthritis, allergies, neoplasia and viral infections.

Potential antagonist compounds include an antibody, or in some cases, an oligopeptide, which binds to the polypeptide. Alternatively, a potential antagonist may be a closely related protein which binds to the receptor which is an inactive form of the polypeptide and thereby prevents the action of the polypeptide of the present invention.

Another antagonist compound is an antisense construct prepared using antisense technology. Antisense technology can be used to control gene expression through triple-helix formation or antisense DNA or RNA, both of which are based on the binding of a polynucleotide to DNA or RNA. For example, the 5' coding portion of the polynucleotide sequence, which encodes for the mature polypeptides of the present invention, is used to design an antisense RNA oligonucleotide of about 10 to 40 base pairs in length. A DNA oligonucleotide is designed to be complementary to a region of the gene involved in transcription, thereby preventing transcription and the production of the polypeptide of the present invention. The antisense RNA oligonucleotide hybridizes to the mRNA in vivo and blocks translation of the mRNA molecule into the polypeptide of the present invention. The oligonucleotides described above can also be delivered to cells so that the antisense RNA or DNA may be expressed in vivo to inhibit production of the polypeptide of the present invention.

Antagonist compounds include a small molecule which binds to the polypeptide of the present invention and blocks its action at the receptor so that normal biological activity is prevented. The small molecules may also bind the receptor to the polypeptide to prevent binding. Examples of small molecules include but are not limited to small peptides or peptide-like molecules.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accordance with published procedures. In addition, plasmids equivalent to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements are used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° are ordinarily used, but may vary in accordance with the supplier's instructions. After digestion, the reaction is electrophoresed directly on a polyacrylamide gel to isolate the desired fragment.

"Oligonucleotides" refer to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments. Unless otherwise provided, ligation may be accomplished using known buffers and conditions with 10 units of T4 DNA ligase ("ligase") per 0.5 μg of approximately equimolar amounts of the DNA fragments to be ligated.

The present invention will be further described with reference to the following examples, however, it is to be understood that the present invention is not limited to such examples. All parts or amounts, unless otherwise specified, are by weight.

6. EXAMPLES

6.1. Example 1

Isolation of cDNAs from cDNA Library Derived from U937 Cell Inhibited by IL-10

6.1.1 Cell Culture

U937 cell lines were maintained in RPMI 1640 medium containing 100U/ml penicillin and 100U/ml streptomycin plus 10% fetal bovine serum. U937 blast cells were propagated every 3–4 days. Cells were collected when the density was about $2\times10^7$ cells per well, centrifuged and washed three times with Hank's solution, then resuspended in RPM11640 medium containing 10% FBS and 10 ng/ml PHA. In the SSH procedure, half of the cells ($1\times10^7$) were stimulated with 10 ng/ml PHA for 8 hours and used as a tester, while the other half ($1\times10^7$) were inhibited with 100 ng/ml IL-10 for 8 hours and used as a driver. mRNAs extracted from the tester and driver U937 cells were used for complementary DNA synthesis.

6.1.2 Synthesis of cDNA

The mRNAs were isolated from U937 cells by using QickPrep® micro mRNA purification kit (Pharmacia). Detailed procedure was carried out under the provided guidelines. Single-stranded as well as double-stranded cDNA were synthesized by using PCR-Select™ cDNA Subtraction Kit (the procedure was carried out under the provided guidelines), during which mRNAs extracted from the tester and driver were used as templates, respectively.

6.1.3 Suppression Subtractive Hybridization (SSH)

Figure 1:
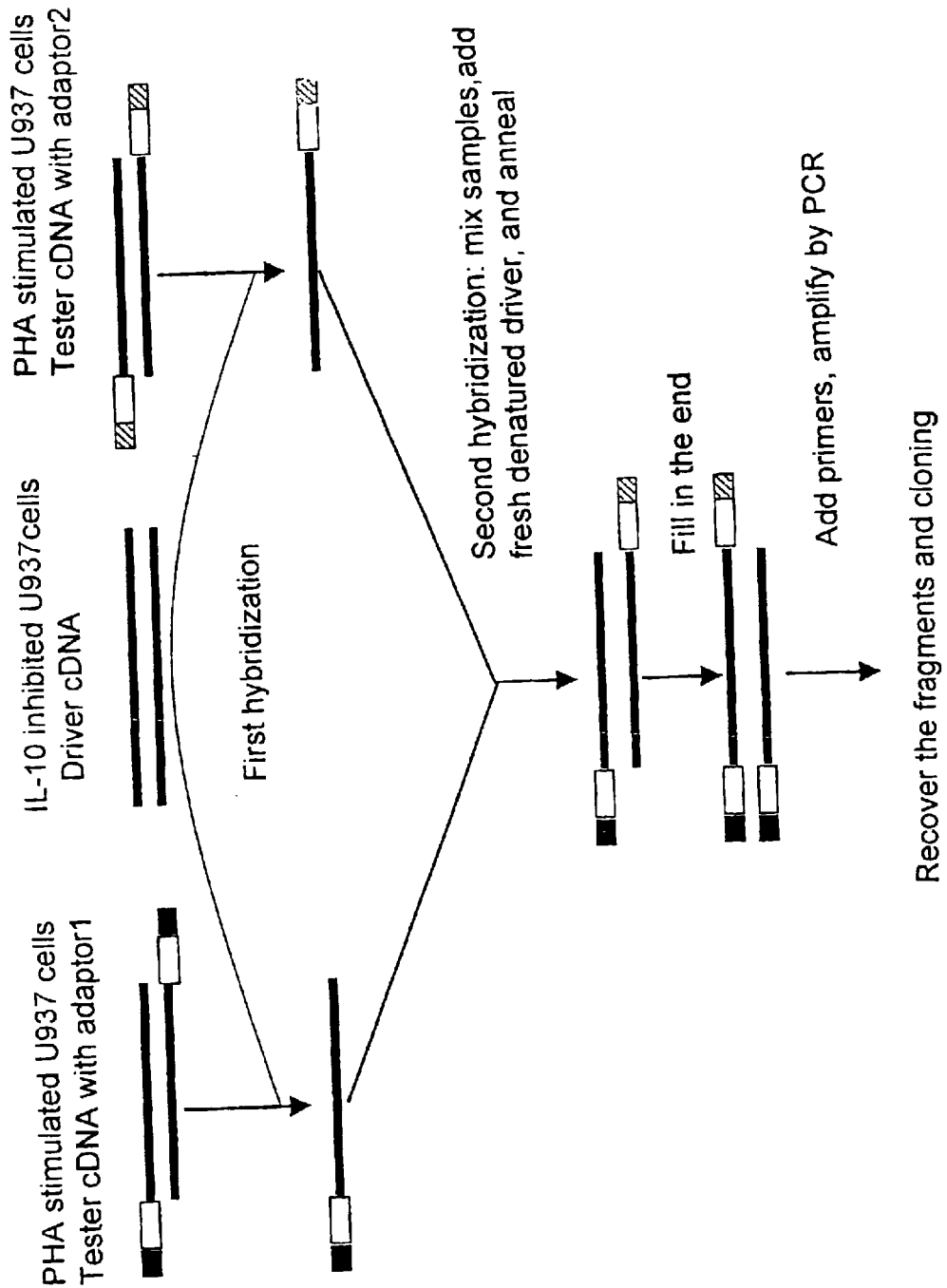

As described in FIG. 1, 2 μg cDNAs of tester and driver were respectively digested with a restrictive enzyme RsaI. The tester cDNA was divided into two groups. Adapter 1 and Adapter 2, provided by the manufacturer, were independently ligated to the two groups of testers. As showed in FIG. 1, the first and second hybridizations were performed, and the resulting annealed material was used as the PCR template. 1 μl of 1:1000 diluted hybridization mixture was amplified for 27 cycles in the first PCR. The primers were provided by the manufacturer. Then, using 1:10 diluted product from the first PCR as a template, the nested P1 and P2 as primers, the second PCR was amplified for 15 cycles. Products of the second PCR contained the fragments of different lengths. The 200–1600 bp fragments were recovered and ligated into the pGEM-T easy vector (Promega). The recombinant vectors were transformed into XL-1 Blue bacteria and white colonies were screened.

6.1.4 DNA Sequencing

The plasmids for sequencing were purified with tip-20 Minipreparation Kit (Qiagen). DNA sequencing was carried out by Dalian Baoshengwu Bioengineering Company by using ALFexpess II DNA sequencer (Pharmacia).

Results

The DNA sequence is shown in SEQ ID NO: 1. The encoding sequence was assembled by overlapping ESTs (Express Sequence Tags) provided by the EST Assembly Machine. The accession number of EST fragments used for the CKLF1 assembly were W38899, N95062, AA429945, AA987264, AA927461, W19056, N89912, AA516431, AA479657, AA455042, AA989129, W52820. The obtained full-length cDNA of CKLF1 has 534 base pair nucleotides, including a poly(A) tail and a polyadenylation signal ATTAAA. The open reading frame of CKLF1 is from nucleotide 152 to nucleotide 448 as showed in SEQ ID NO: 1, which encodes a polypeptide which has 99 amino acid residues. The homology analysis was conducted through GenBank on World Wide Web. The GenBank access (registration) number of CKLF1 is AF096895.

The characteristics of CKLF1 amino acid (as set forth in SEQ ID NO: 2) were analyzed with softwares PcGene, Prosite and Signal P server provided by the World Wide Web site. The result shows there is a CC motif in CKLF1 amino acid, which is characteristic of the C—C chemokine subfamily. The first amino acid residue of the deduced mature polypeptide is glycine. The deduced CKLF1 protein has no typical signal cleavage site, no transmembrane domain, no DNA binding site and no putative N-glycosylation site. The first 17 amino acid residues of the N-terminal are hydrophobic and are the possible signal peptide. The homology analysis showed that the CKLF1 polypeptide shares no obvious homology with known proteins; amino acid 35 through 79 shares 46 percent homology with the permease of *Caenorhabditis elegans*.

6.2. Example 2

Cloning of CKLF2, CKLF3 and CKLF4

The 5' oligonucleotide primer 1 (P1, SEQ ID NO: 9) and 3' oligonucleotide primer 2 (P2, SEQ ID NO: 10) were designed according to the coding sequence of the CKLF1 polynucleotide. The sequences are shown as follows: P1, SEQ ID NO: 9: 5'ATG GAT AAC GTG CAG CCG AAA AT 3', P2, SEQ ID NO: 10: 5'CCG CTC GAG TTA CAA AAC TTC TTT TTT 3'.

In the semi-quantitative PCR, the cDNA library from the PHA-stimulated U937 cells as well as the cDNA library from the PHA-stimulated and IL-10 inhibited U937 cells were used as templates, respectively; P1 and P2 were used as primers. The amplification condition is as follows: 94°, 2 minutes; 94°, 15 seconds, 58°, 15 seconds, 72°, 30 seconds; 30 cycles; 72°, 7 minutes.

Results

From the two cDNA libraries, PCR products with different lengths were obtained and cloned into pGEM-T Easy vector. By using the DNA sequencing method as described above, new sequences were identified, such as CKLF2, CKLF3 and CKLF4, as shown in SEQ ID NO:3, SEQ ID NO:5 and SEQ ID NO:7, respectively. The GenBank accession numbers of CKLF2, CKLF3 and CKLF4 are AF135380, AF135381 and AF145216, respectively.

Figure 2:
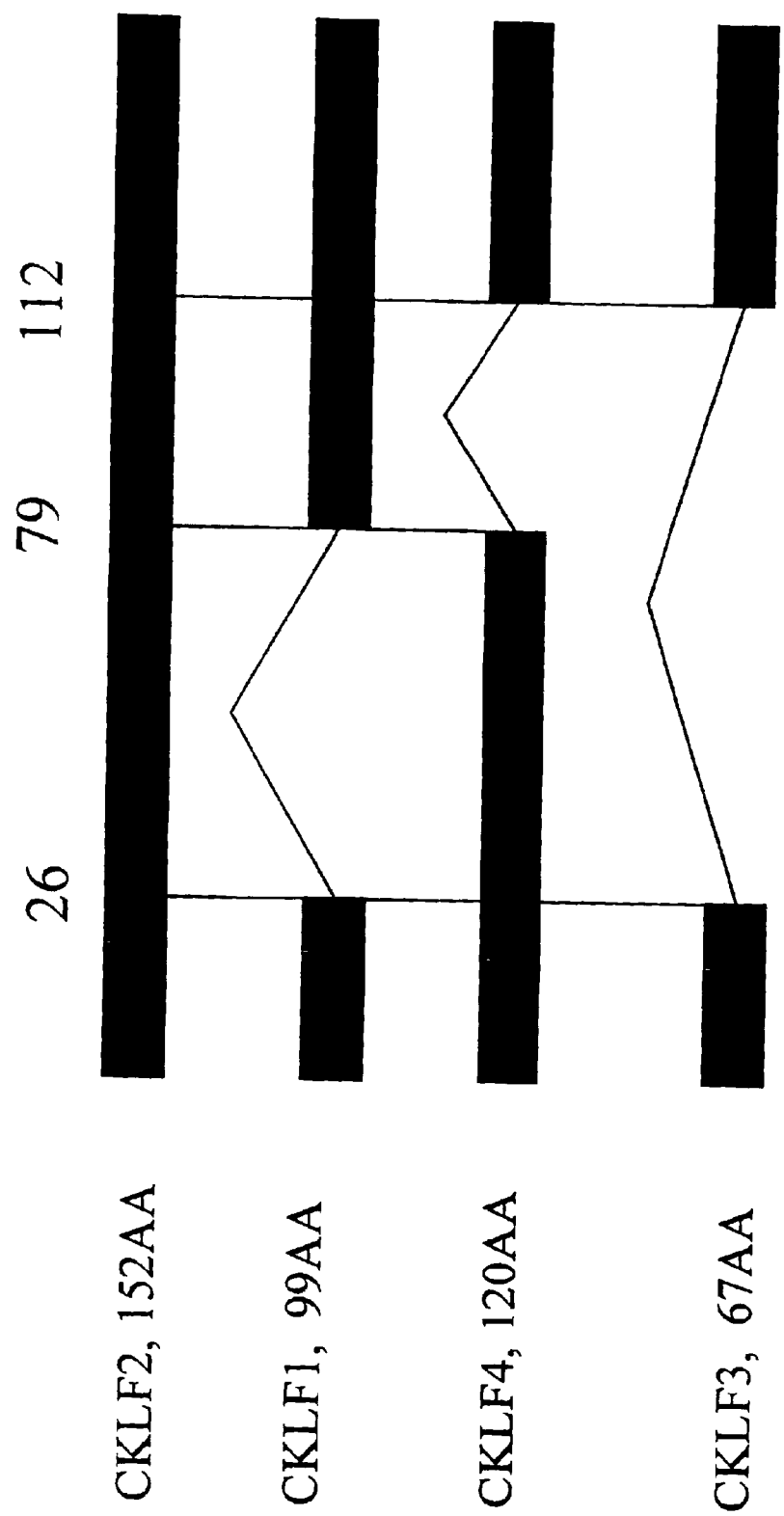
FIG. 2 shows the structural differences of CKLF1, CKLF2, CKLF3 and CKLF 4.

As revealed in FIG. 2, the polynucleotides of CKLF2, 3, 4 have no frameshift mutation compared with that of CKLF 1 (SEQ ID NO: 1). The CKLF2 polynucleotide encodes a polypeptide with 152 amino acid residues as shown in SEQ ID NO:4. The CKLF3 polynucleotide encodes a polypeptide with 67 amino acid residues as shown in SEQ ID NO:6. The CKLF4 polynucleotide encodes a polypeptide with 120 amino acid residues as shown in SEQ ID NO:8. The CKLF3 polypeptide has conservative amino-terminal and carboxyl-terminal sequences. CKLF2 and CKLF4 have different exons from each other. The PcGene analysis shows that the CKLF2 and CKLF4 polypeptides have transmembrane domains. It is assumed that CKLF2, 3 and 4 polypeptides probably result from different splicing processes of CKLF1 mRNA.

6.3. Example 3

Northern Blot Analysis of CKLF1 mRNA Expression in U937 Cells

Total RNA was extracted using GIBCO-BRL TRI$_{ZOL}$™ reagent (GIBCO-BRL). 1×10$^7$ tester and driver U937 cells were collected by centrifugation, respectively, and 1 ml TRI$_{ZOL}$™ reagent was added to lyse the U937 cells. Centrifugation was then carried on after adding 0.2 ml chloroform. The total RNA was precipitated with isopropanol and washed with ethanol. The dried RNA was resuspended with RNase free H$_2$O and quantified with a spectrophotometer (Beckman, 640 nm).

The RNA sample was mixed with 5×RNA loading buffer at the ratio 4:1 (volume vs. volume). The mixture was incubated at 65° for three to five minutes and then placed on ice immediately. In this experiment, the total RNAs of tester and driver (20 μg per well) were fractionated on 1.2% agarose formaldehyde gel under the voltage of 5–7 V/cm, and then transferred onto GeneScreen-plus nylon membrane by capillary transfer.

The template for labeling the CKLF1 probe used for Northern blot was the EST fragment obtained from SSH. The procedures for labeling probe and hybridization was performed according to the protocol of Random Primer Fluorescein Labeling Kit with anti-fluorescein HRP (DUPONT NEN, Boston, Mass.) provided by the company.

Results

Figure 3:
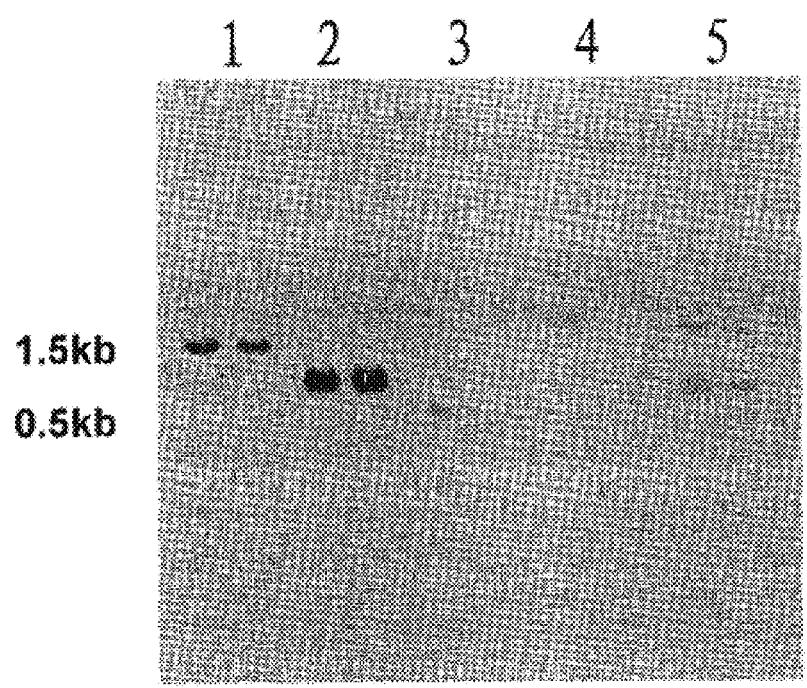
FIG. 3 shows the Northern blot analysis of CKLF1 mRNA expression in U937 cells.

As shown in FIG. 3, the CKLF1 gene is about 0.5 kb long. The expression level of CKLF1 was high in PHA-stimulated U937 cells, and IL-10 inhibited the expression of CKLF1.

6.4. Example 4

Expression of CKLF1 in Prokaryotic Cells 6.4.1 Construction of Prokaryotic Expression Vector The 5' oligonucleotide primer 1' (P1', SEQ ID NO: 11) and the 3' oligonucleotide primer 2' (P2', SEQ ID NO: 12) were designed according to the cDNA sequence of CKLF1. The 3' primer contains a complementary sequence to the XholI site. The primers are as follows:

P1', SEQ ID NO: 11: 5'CTG ATA CCA GAA ACC ACA ACA TT 3'

P2', SEQ ID NO: 12: 5'GGA AGA ATA CAG AAA TAT GTT TAA TAC 3'

CKLF1 fragment was amplified by using P1' and P2' as PCR primers, and plasmid pGEM-T easy-CKLF1 as the template. The PCR products were blunted by klenow enzyme and digested with the endonuclease XholI. After purified on a 1% agarose gel, the fragment was ligated with the pMTY4 plasmid which had been digested by endonucleases StuI and XholI. The recombinant plasmid was designated as pMTY4-CKLF1.

6.4.2 Expression and Purification of CKLF1

The *Escherichia coli* (*E. coli*) strain pop2136 harboring the prokaryotic expression vector pMTY4-CKLF1 was induced under a temperature of 42° to express the MS2-CKLF1 fusion protein in the form of an inclusion body. MS2 and CKLF1 polypeptides were linked by thrombin peptide. Bacteria were collected and the inclusion body was lysed by supersonic method. The inclusion body was denatured in a 20 mM Glycin-NaOH (pH10.0) solution containing 8M urea at 37° for 30 minutes, renatured by diluting the concentration of urea to 1M, then cleaved with thrombin at 25° overnight. CKLF1 mature protein was purified by ion exchange chromatography with Q Sepharose Fast Flow. The cleaved CKLF1 protein was then loaded into the column in 20 mM Glycin-NaOH (pH10.0) buffer. The column was washed with 50 mM Tris-HCl(PH8.9) and the target protein was eluted in 0.04 M NaCl solution.

Results

Figure 4:
FIG. 4 is the result of SDS-PAGE gel stained with Coomassie blue, which shows the expression of recombinant plasmid pMTY4-CKLF1 in E. coli.
Figure 5D:
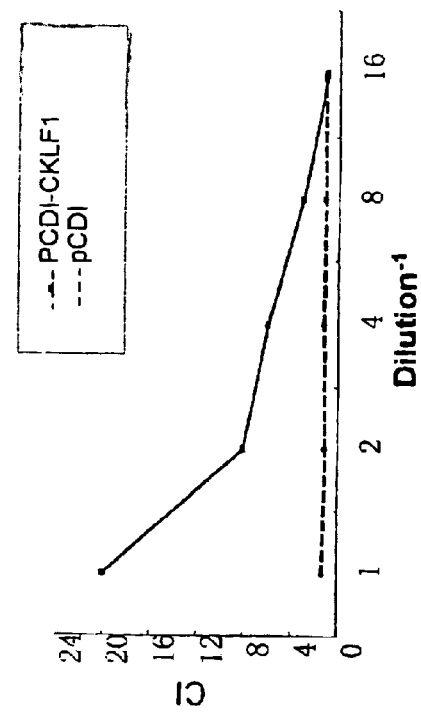
Figure 5E:
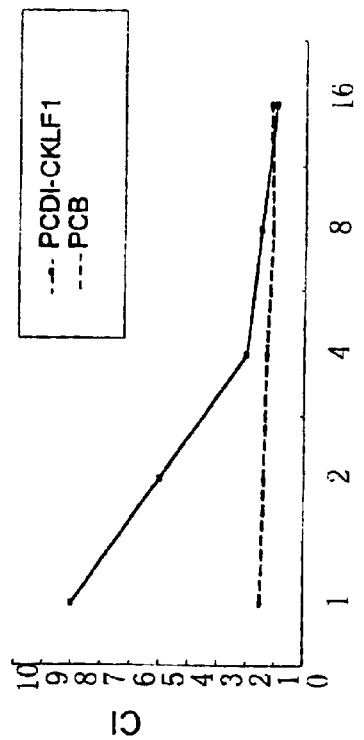
Figure 5F:
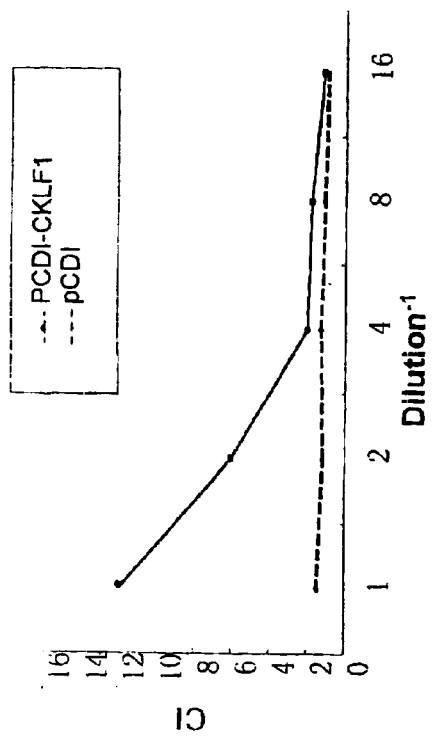
Figure 5G:
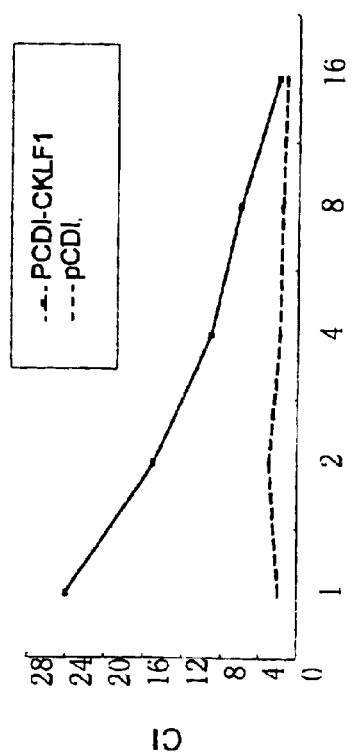
Figure 5I:
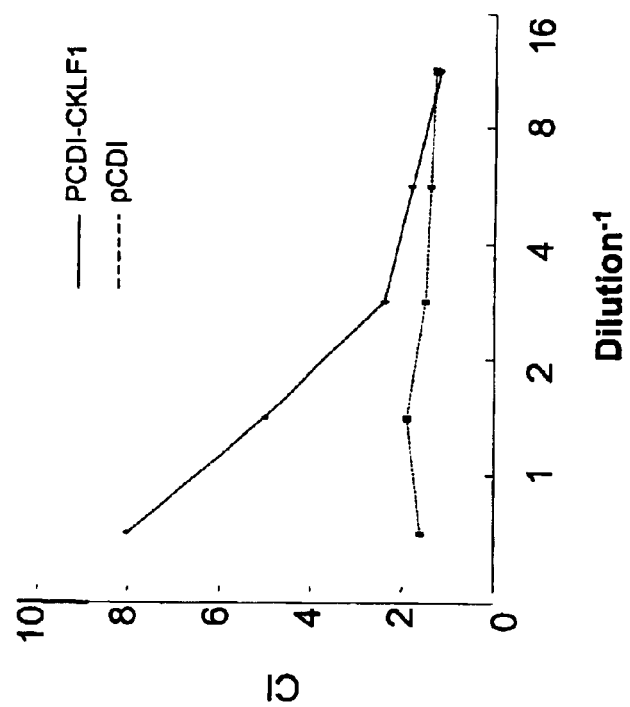
Figure 5H:
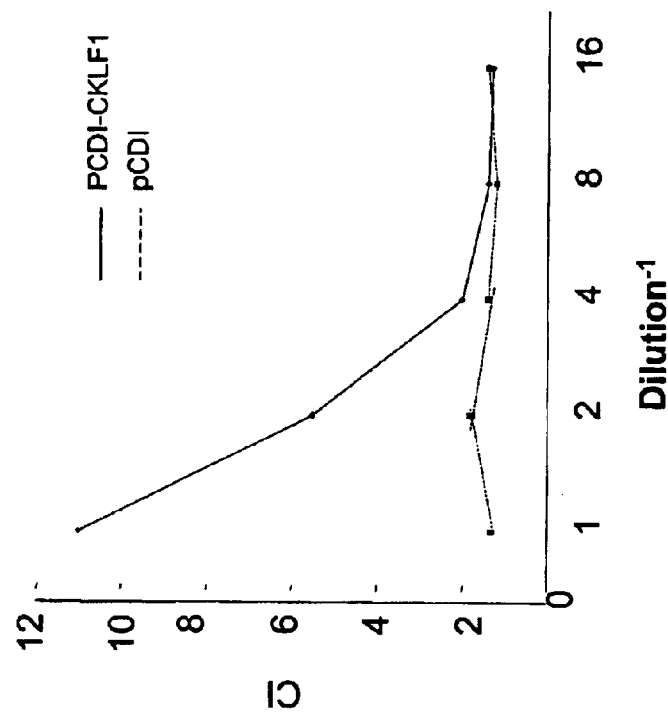

As shown in FIG. 4, the MS2-CKLF1 fusion protein expressed in *Escherichia coli* with high level and took in about 30 percent of the total proteins expressed by the bacteria. Furthermore, it was found that the ratio of dimmer protein (protein consisting of two polypeptide chains) vs monomer protein (protein consists of a single polypeptide chain) is about 1:4.

6.5. Example 5

Subcellular Localization of CKLF1, 2, 4

The coding regions of CKLF1, 2 and 4 were amplified by using primer 1 (P1) and primer 5 (P5, SEQ ID NO: 13: 5' CGG GAT CCA AAA CTT CTT TTT TTT CAT GC 3'). In the coding region of CKLF1, 2 and 4, the stop codon was removed and a BamHI site was introduced near the 3' end. The PCR products were blunted by klenow enzyme and then digested with BamHI. The pEGFP—N1 expression vector (CLOTECH) was digested with EcoRI, blunted with klenow enzyme and then digested with BamHI. After purification and recovery from the agarose gels, the fragments were ligated into the digested vectors. The recombinant plasmids were designated pEGFP-CKLF1, 2 and 4, respectively. The coding sequences of CKLF1, 2 and 4 were the same as the open reading frame of EGFP.

Recombinant plasmids pEGFP-CKLF1, 2 and 4 were purified and transfected into Hela cells using Superfect Transfection Reagent (Qiagen). After 72 hours, the cells were washed with PBS three times and then fixed in 4% paraformaldehyde for 30 minutes. Cells were washed again with PBS and detected by a fluorescence microscope.

Results

In cells expressing the CKL 1/EGFP fusion protein, weak fluorescence was detected throughout the cells, which means that most of the CKLF1/EGFP fusion protein was secreted into the supernatants. Both this result and that of the bioactivity of CKLF1 polypeptide in the supernatants of COS-7 cells indicated that CKLF1 was a secreted protein. As for pEGFP-CKLF2 and pEGFP-CKLF 4, the fluorescence is predominantly detected on the cell membrane.

6.6. Example 6

The Chemotactic Activity of CKLF1

6.6.1 Cell Lines

K562 is a human chronic myelogenous leukemia cell line; U937 is a human promonocytic cell line; TF-1 is human erythroleukemia cell line; HL-60 is a human acute promyelocytic leukemia cell line. HL-60 cells differentiated into neutrophils after culture in the normal RPMI 1640 medium containing 1.3% dimethyl sulfoxide (DMSO) for about 4 days.

Separation of neutrophils, lymphocytes and monocytes from periphery blood mononuclear cells (PBMC) is described as follows. 12 ml of periphery blood from healthy volunteers is mixed with the final concentration of 25–50 u/ml heparin and 2 volumes of Hank's solution, mixed briefly and then added to a half volume of Ficoll-Hypaque (1.077 g/cm$^3$). After centrifugation for 25 minutes at 2,000 rpm at 4° C., the mononuclear cells between the upper plasma and the lower Ficoll-Hypaque are isolated and resuspended in RPMI 1640, which are cultured at 37° for 30 minutes. The non-adherent cells are lymphocytes and the adherent monocytes are obtained by digestion with 0.5% EDTA. The neutrophils above the erythrocyte layer are purified by lyses with ammonium chloride (pH7.2) to eliminate the contaminating erythrocytes.

6.6.2 Chemotaxis Assay

The coding sequence of CKLF1 was released from pGEM-T easy-CKLF1 plasmid by using endonuclease EcoRI and subcloned into the pCDI vector digested with endonuclease EcoRI. The recombinant pCDI-CKLF1 expression plasmid was constructed. The plasmid pCDI was used as a control; pCDI and pCDI-CKLF1 plasmids were transfected into COS-7 cells. Supernatants were collected and diluted for chemotactic analysis. The purified cells were adjusted to 1×10$^6$/ml and loaded into the upper wells of the chamber. Neutrophils were incubated for 1 hour and other cells were incubated for 3 hours. Then the membrane was taken from the chamber and the nonspecific cells were scraped. Migrated cells were fixed with methanol and stained with Giemsa. Migrated cells were counted microscopically at 400× magnification in five randomly selected fields per well. The data of chemotactic activity of CKLF1 are expressed as chemotactic index (CI, the ratio between the number of cells migrated in the supernatants of transfected cells and the number of cells migrated in the supernatants of the non-transfected cells).

Results

As illustrated in FIGS. 5A–5I, the supernatants of pCDI-CKLF1-transfected cells have obvious chemotactic effect on human neutrophils, monocytes, U937 cells, K562 cells, DMSO-stimulated HL-60 cells, mouse peritoneal macrophages and lymphocytes, but have no chemotactic activity on TF-1 cells, NFS-60 cells or non-stimulated HL-60 cells. This reveals that CKLF1 is a secreted protein with broad-spectrum chemotactic activity. Strong reductant DTT can entirely block the chemotactic activity of CKLF1. In addition, the chemotactic effect of CKLF1 is dose-dependent.

6.7. Example 7

The Enhancing Effect of CKLF1, 2 and 3 on the Proliferation of Mouse Marrow Cells

6.7.1 Construction of Eukaryotic Expression Vectors

The eukaryotic expression vector pCDI was constructed by substituting the BglII-KpnI fragment of plasmid pCDNA3 (Invitrogen) with the BglII-KpnI fragment of plasmid pCI (Promega).

Figure 6:
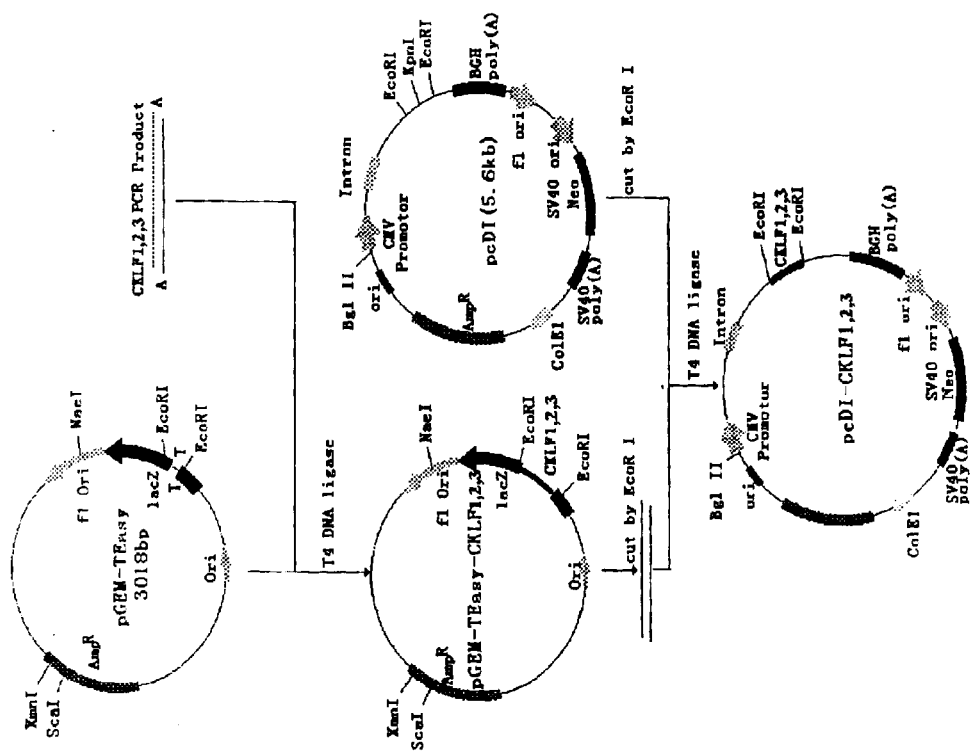
FIG. 6 depicts the process of constructing mammalian express vector pCDI-CKLF1. Construction of plasmids pCDI-CKLF2, pCDI-CKLF3 and pCDI-CKLF 4 is similar to that of pCDI-CKLF1.

The polynucleotide of CKLF1 was amplified from PHA-stimulated U937 cell cDNA library with primer P1 and P2 and cloned into pGEM-T easy vector. The inserted gene was released after EcoRI digesting and was subcloned into the EcoRI site of the mammalian expression vector pCDI. The sense clones were selected and the recombinant plasmid was designated as pCDI-CKLF1. The construction of recombinant plasmids pCDI-CKLF 2 and pCDI-CKLF 3 were similar to pCDI-CKLF1 (FIG. 6). The purified plasmids were transfected into COS-7 cells using Superfect Transfection Reagent (Qiagen) and the supernatants were collected for biological analysis.

6.7.2 Cell Proliferation Assay Using MTT Method

Bone marrow cells were obtained from BALB/c mice. After lysed with ammonium chloride(pH7.2) to remove contaminating erythrocytes, the density of bone marrow cells were adjusted to 1.5×10$^6$/ml. 90 µl of the cell suspension was plated in each well of 96-well microplate. Supernatant of non-transfected COS-7 cells was used as a negative control, while COS-7 supernatant with 100 ng/ml of IL-3 and 100 ng/ml of SCF was used as positive control. 10 µl supernatant of COS-7 cells transfected with pCDI-CKLF1, 2, 3 were added to the sample groups, respectively. Every group contained 6 wells. Cells were cultured in 5% CO$_2$ at 37° for 90 hours, then, 10 µl MTT with a concentration of 10 mg/ml was added to each well. After continuing the culture for six hours, lysis buffer (50% DMSO, 20% SDS, PH4.4) was added and the absorption value of each well was measured at 570 nm using the ELISA-reader.

Results

Figure 7:
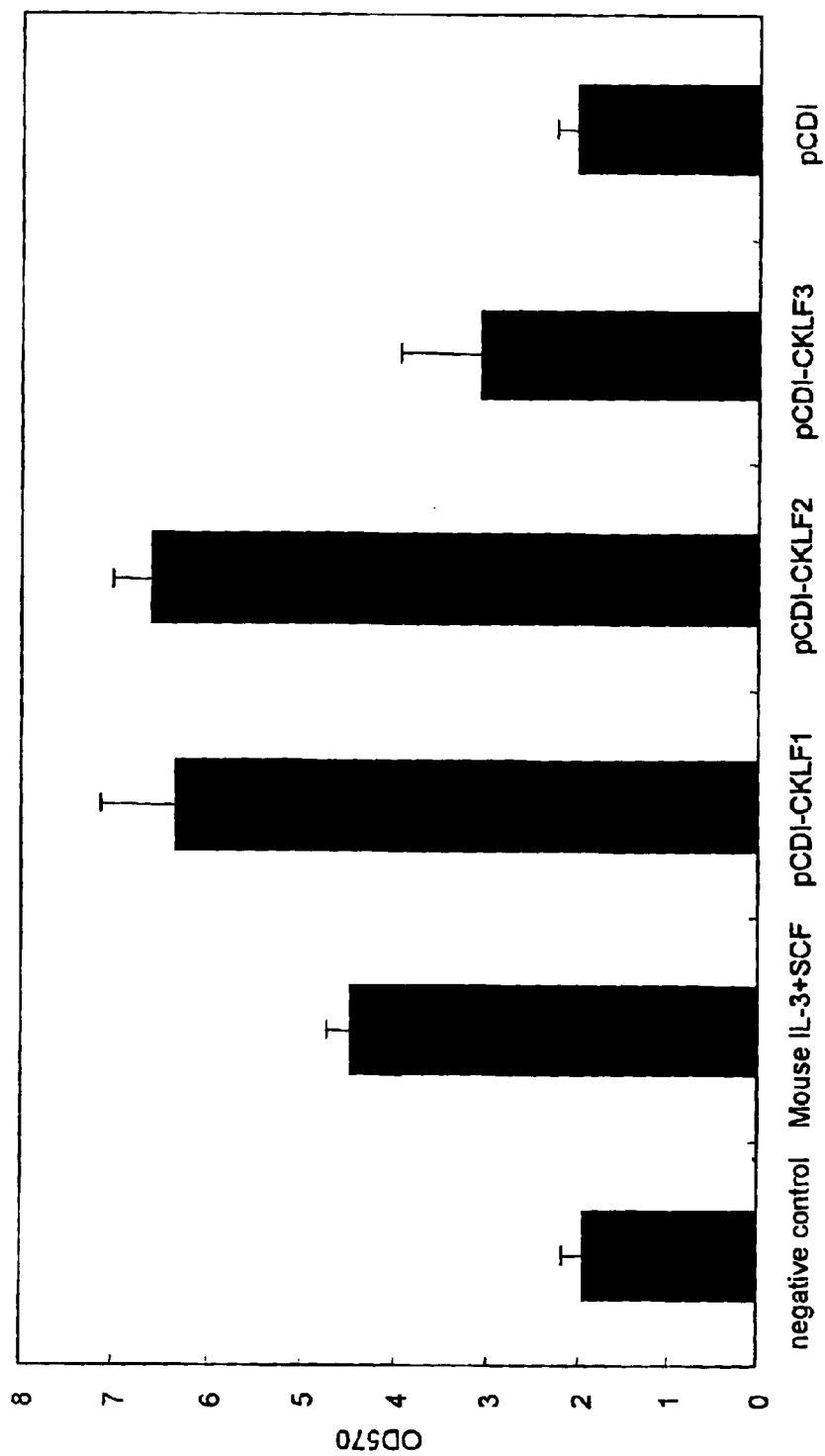
FIG. 7 depicts the proliferation effect of recombinant CKLF1, 2, 3 to mouse bone marrow cells.

As shown in FIG. 7, the supernatants of pCDI-CKLF1, 2 transfected cells have an obvious promoting effect on the proliferation of mouse bone marrow cells, while the effect of the supernatants of pCDI-CKLF3 is weaker. When cells were cultured for 72 hours, there was no obvious difference between different cell samples, some cells dying naturally. After continuing the culture until 80 hours, some round, medium-sized cells appeared in the wells containing pCDI-CKLF1 or pCDI-CKLF2 supernatants. Such cells were scarce in the wells containing pCDI-CKLF3 supernatants. Cell shape and quantity in the wells containing pCDI-CKLF3 supernatants were similar with that of the control group, which was shown in FIGS. 8A and 8B.

6.8. Example 8

The Enhancing Effect of CKLF1 on the Growth of Normal Human Low-Density Bone Marrow Cells

6.8.1 Stimulating Effect On Cell Proliferation

Low-density bone marrow cells were separated from bone marrow of young healthy adults using density cut separation on Ficoll-Hypaque ($1.077\pm0.002/cm^3$). The separated and purified marrow cells were adjusted to $2\times10^6$/ml, 90 µl of which was plated into each well of 96-well microplate. 10 µl supernatants of pCDI-CKLF1 transfected COS-7 cells were added to the wells to analyze the effect of CKLF1, while 10 µl supernatants of 72-hour-cultured non-transfected COS-7 cells were added as negative control and rhGM-CSF was used as positive control with the final concentration of 10 ng/ml. The cell proliferation rate was tested by MTT method as described above.

Results

As shown in FIG. 9, the supernatants of pCDI-CKLF1 transfected COS-7 cells with 10 times dilution can promote the proliferation of bone marrow cells compared with the control supernatants. The promoting activity is similar to that of rhGM-CSF with its final concentration 10 ng/ml.

6.8.2 Stimulatory Effect Of CKLF1 On Colony Formation

Normal human low density bone marrow cells were adjusted to $5\times10^4$/ml after density cut separation on Ficoll-Hypaque ($1.077$ g/cm$^3$). The cell suspensions were seeded in 0.3% soft agar. Supernatants of pCDI-CKLF1 transfected COS-7 cells with different dilution were added. Supernatants of the control vector pCDI transfected COS-7 cells were used as a negative control and GM-CSF with final concentration of 100 ng/ml was used as a positive control. The volume balance among different samples was made up with RPMI1640 medium. After two weeks of culturing in 5% $CO_2$ at 37°, colonies which contain more than 50 cells were counted.

Results

As described in Table 1, the supernatants containing CKLF1 can boost the colony formation of human low-density marrow cells and have an obvious cooperative effect with 100 ng/ml GM-CSF. Among the CKLF1-stimulated marrow cells, giant cells are found, as shown in FIG. 10, whose survival period is longer than that of cells stimulated with GM-CSF only.

TABLE 1

Stimulating effect of CKLF1 on the granulocyte-monocyte colony formation of human low density bone marrow cells

| Concentration | GM-CSF | pCDI | CKLF1 | GM-CSF + CKLF1 | GM-CSF + CKLF1 |
|---|---|---|---|---|---|
| $10^{-1}$ | 22 ± 3 | 11 ± 2 | 28 ± 3 | 21 ± 2 | 36 ± 3 |
| $15^{-1}$ |  | 11 ± 1 | 16 ± 2 | 23 ± 1 | 28 ± 2 |
| $30^{-1}$ |  | 10 ± 3 | 10 ± 2 | 20 ± 2 | 22 ± 2 |

6.9. Example 9

Expression of CKLF1 and Its Variants in Normal and Tumor Tissues

The expression level of CKLF1 and its variants in the fetal, adult and tumor tissues were analyzed by using Multiple Tissue cDNA Panel (Clontech). The one-stranded cDNA libraries were used as templates and P1 and P2 were used as primers. The reaction condition was the same as described above.

Results

As illustrated in FIGS. 11A and 11B, the expression levels of CKLF1 and its variants were lower in normal adult tissues and could hardly be detected in prostate and pancreas tissue. CKLF1 and CKLF2 have a high level of expression in fetal and tumor tissues such as breast, colon, lung, ovary, pancreas and prostate carcinoma, while the expression level of CKLF3 and CKLF4 is lower in fetal and tumor tissues (FIGS. 11C–11D), which suggest that CKLF1 may have a close relationship with fetal development and tumorgenesis.

6.10. Example 10

Biological Activity of CKLF1 In Vivo

BABL/c mice, 4–6 weeks old, were purchased from the Genetic Institution of China Academy of Medical Science. The plasmids pCDI and pCDI-CKLF1 were purified by tip-10000 Giga-preparation Kit (Qiagen). Each mouse in the pCDI-CKLF1 group was injected with 100 µl pyrogen-free physiological saline containing 100 µg pCDI-CKLF1 in anterior tibial muscle or subcutaneous tissue, while the control group was treated with the same physiological saline containing 100 µg pCDI, using bupivacaine or electric pulse (40 ms, 80 v) to enhance the absorbance of DNA. On the 10th and the 30th day after injection, mice were killed and the injection sites were excised. Samples of muscle biopsies were analyzed by staining with Fuelgen, ACP and HE, respectively, and then observed under a microscope. The bioactivity of CKLF1 on the local injection site was analyzed by histological, immunohischemical and enzymological methods.

Results

The function of the pCDI-CKLF1 polypeptide is: (1) attracting inflammatory cells to the injection sites; (2) boosting the proliferation and differentiation of skeletal muscle cells; (3) promoting the proliferation and differentiation of keratinocytes of follicles.

The results of the ACP (FIGS. 12A–12B) and HE staining showed that there were no obvious structural and morphological changes between the cells in the control group (cells injected with 0.9% physiological saline containing the pCDI plasmid) and the normal mice skeletal muscle cells. While in the pCDI-CKLF1 group, more nuclei appeared in the middle of muscle fiber tissues, ranked like a string of beads, accompanied by the appearance of monocyte-macrophage infiltration. Such phenomena were observed at 10, 20 and 30 days after injection (especially remarkable at 10 days after injection).

The result of Feulgen staining showed that by using the Leica Q500MC analyzer, the mean optical density (MOD) of cells in the pCDI-CKLF1 group was much higher than those in the pCDI control group, (Table 2), which indicates that there were more nuclei in the muscle tissues. The increase of nuclei was more evident in the muscles injected with pCDI-CKLF1 plus needling (t test $p<0.01$).

TABLE 2

Analysis of the result of Feulgen saining of the
injected skeletal muscular tissue (x ± s, unit MOD)

| Plasmid | pCDI-CKLF1 (experimental group) | | pCDI (control group) | |
|---|---|---|---|---|
| Group | A | B | A | B |
| Quantity of nucleus | 514.33 ± 32.18 | 666.7 ± 42.51 | 67.18 ± 11.21 | 63.43 ± 14.34 |
| MOD | 0.134 ± 0.017 | 0.118 ± 0.023 | 0.098 ± 0.008 | 0.094 ± 0.001 |

Notice: A is bupivacaine injection + muscle injection(IM), B is IM+ needling

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entireties.

What is claimed is:

1. An isolated polynucleotide comprising a member selected from the group consisting of:
   (a) a polynucleotide encoding the polypeptide consisting of the amino acid sequence as set forth in SEQ ID NO:2; and
   (b) a polynucleotide encoding a mature polypeptide consisting of the amino acid sequence expressed by the cDNA contained in CGMCC Deposit NO.0392.

2. The polynucleotide of claim 1, wherein the polynucleotide is cDNA.

3. The polynucleotide of claim 2 having the sequence as set forth in SEQ ID NO:1.

4. The polynucleotide of claim 3 consisting of the sequence as set forth in SEQ ID NO:1.

5. A vector containing the cDNA of claim 2.

6. The vector of claim 5 containing (a) the sequence as set forth In SEQ ID NO:1, or (b) the cDNA contained in CGMCC Deposit NO. 0392.

7. A host cell being transformed, transducted or transfected with the vector of claim 5.

8. The host cell of claim 7 containing (a) the sequence as set forth in SEQ ID NO:1, or (b) the cDNA contained in CGMCC Deposit NO. 0392.

9. The host cell of claim 7, wherein the host cell is one member selected from the group consisting of bacterium, fungal cell, insect cell, animal cell and adenovirus cell.

10. A method of producing a chemokine-like factor polypeptide comprising introducing the vector of claim 5 into a host cell, and expressing from the host cell or extracellular media the polypeptide encoded by said cDNA.

11. The method of claim 10, wherein the vector contains (a) the sequence as set forth in SEQ ID NO:1, or (b) the cDNA contained CGMCC Deposit NO. 0392.

12. The method of claim 11, wherein the host cell is one member selected from the group consisting of bacterium, and animal cell.

13. The polynucleotide of claim 1, wherein the polypeptide consists of the amino acid sequence as set forth in SEQ ID NO:2.

14. The polynucleotide of claim 1, wherein the polypeptide consists of the amino acid sequence expressed by the cDNA contained in CGMCC Deposit NO. 0392.

15. The polynucleotide of claim 1, wherein the polypeptide has chemotatic and hematopoletic stimulating activities.

16. The polynucleotide of claim 1, wherein the polynucleotide is RNA.

17. An isolated polynucleotide fragment of the sequence as set forth in SEQ ID NO:1 or the complement thereof that hybridizes to the sequence as set forth in SEQ ID NO:1 under wash conditions of 125 mM sodium phosphate (pH7.2), 0.05 mM EDTA, and 2.5% SDS at 65° C., wherein said fragment is at least 20 nucleotides in length.

18. The polynucleotide fragment of claim 17, wherein the polynucleotide fragment is cDNA.

19. A vector containing the polynucleotide fragment of claim 17.

20. A host cell being transformed, transducted or transfected with the vector of claim 19.

21. The host cell of claim 20, containing said polynucleotide fragment.

22. The host cell of claim 21, wherein the host cell is one member selected from the group consisting of bacterium, fungal cells insect cell, animal cell and adenovirus cell.

23. The polynucleotide of claim 17, wherein the polynucleotide fragment is RNA.

* * * * *